United States Patent
Nishiyama et al.

(10) Patent No.: US 11,707,530 B2
(45) Date of Patent: Jul. 25, 2023

(54) LIGAND CAPABLE OF MULTIVALENTLY BINDING TO GLUTAMINE TRANSPORTER, AND COMPOSITION COMPRISING SAME

(71) Applicants: TOKYO INSTITUTE OF TECHNOLOGY, Tokyo (JP); OSAKA UNIVERSITY, Osaka (JP)

(72) Inventors: Nobuhiro Nishiyama, Tokyo (JP); Hiroyasu Takemoto, Tokyo (JP); Takahiro Nomoto, Tokyo (JP); Keishiro Tomoda, Tokyo (JP); Makoto Matsui, Tokyo (JP); Naoki Yamada, Tokyo (JP); Yuto Honda, Tokyo (JP); Hideshi Ishii, Osaka (JP); Masaki Mori, Osaka (JP); Masamitsu Konno, Osaka (JP)

(73) Assignees: TOKYO INSTITUTE OF TECHNOLOGY, Tokyo (JP); OSAKA UNIVERSITY, Osaka (JP)

( * ) Notice: Subject to any disclaimer, the term of this patent is extended or adjusted under 35 U.S.C. 154(b) by 1144 days.

(21) Appl. No.: 16/326,657

(22) PCT Filed: Aug. 17, 2017

(86) PCT No.: PCT/JP2017/029552
§ 371 (c)(1),
(2) Date: Feb. 19, 2019

(87) PCT Pub. No.: WO2018/037996
PCT Pub. Date: Mar. 1, 2018

(65) Prior Publication Data
US 2021/0308271 A1     Oct. 7, 2021

(30) Foreign Application Priority Data

Aug. 22, 2016   (JP) .................. 2016-161774

(51) Int. Cl.
*A61K 47/64*   (2017.01)
*A61K 49/14*   (2006.01)

(52) U.S. Cl.
CPC ........ *A61K 47/6455* (2017.08); *A61K 49/146* (2013.01)

(58) Field of Classification Search
CPC .. A61K 47/6455; A61K 49/146; A61K 47/32; A61K 47/34; A61K 47/42; A61K 47/66; A61K 49/00; A61K 49/14; A61K 45/00; A61P 35/00
See application file for complete search history.

(56) References Cited

PUBLICATIONS

Li et al, Colloids and surfaces B: Biointerfaces, 2016, 141, 260-267 (Year: 2016).*
Lin Li, et al; Large amino acid transporter 1 mediated glutamate modified docetaxel-loaded liposomes etc.; Colloids and Surfaces B: Biointerfaces; 2016; vol. 141, p. 260-267.
N. Yamada, et al; Engineering Tumour Cell-Binding Synthetic Polymers w/Sensing Dense Transporters Assoc.w/ Aberrant Glutamine Metabolism; Scientific Rpts.; 2017; vol. 7;p. 1-10.
Alves, et al.; A platinum Chugaev carbene complex as a potent anticancer agent; Chem. Commun.; 2011; 47; 7830-7832.
Mah, et al.; Lead(II) Complex Formation with Glutathione; Inorganic Chemistry; vol. 51; 2012; 6285-6298.

* cited by examiner

*Primary Examiner* — Sudhakar Katakam
(74) *Attorney, Agent, or Firm* — Kilpatrick Townsend & Stockton LLP

(57) ABSTRACT

The present invention pertains to a ligand that contains a plurality of groups represented by formula (1) and is capable of multivalently binding to a glutamine transporter expressed in excess in a cancer cell compared to a normal cell.

8 Claims, 15 Drawing Sheets

FIG. 9
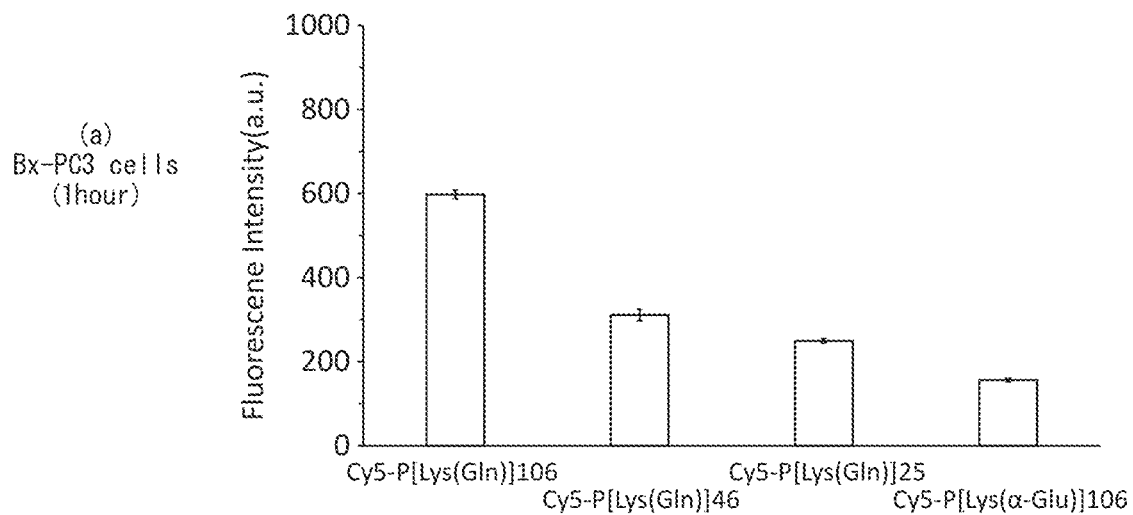
(a) Bx-PC3 cells (1hour)
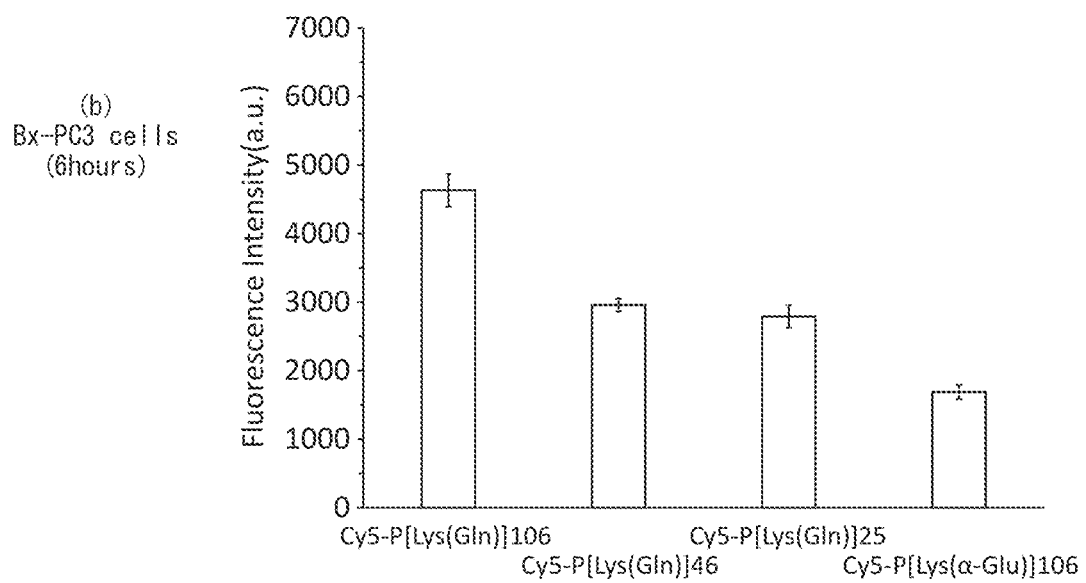
(b) Bx-PC3 cells (6hours)

FIG. 10
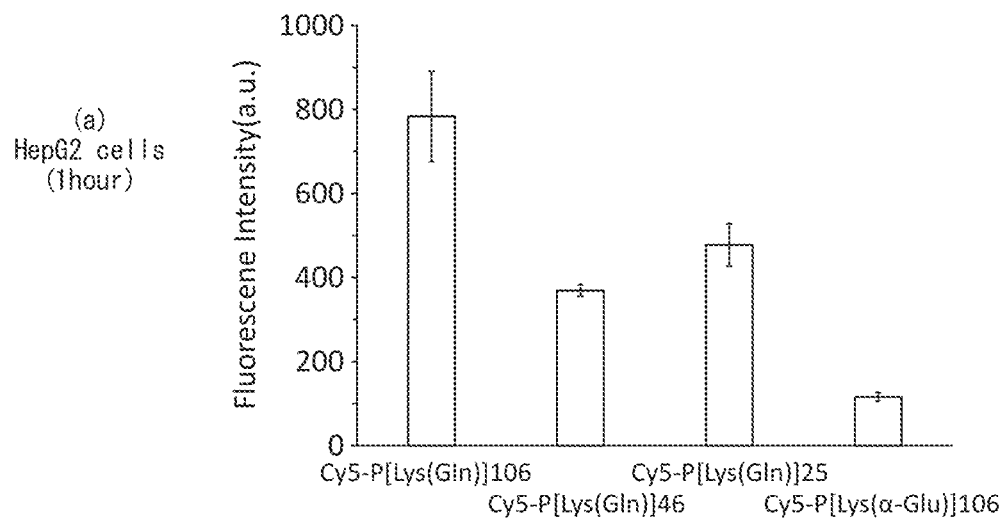
(a) HepG2 cells (1hour)
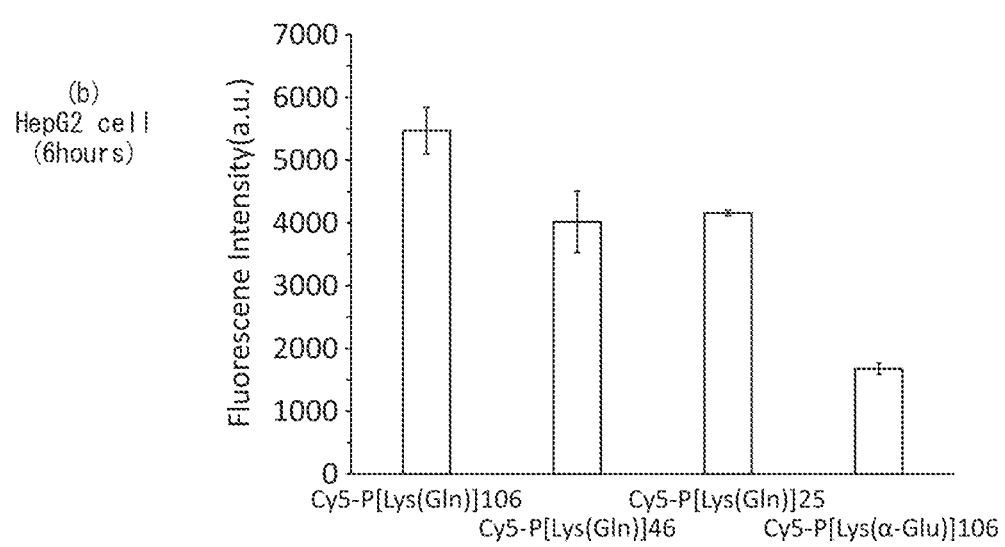
(b) HepG2 cell (6hours)

LIGAND CAPABLE OF MULTIVALENTLY BINDING TO GLUTAMINE TRANSPORTER, AND COMPOSITION COMPRISING SAME

CROSS-REFERENCE TO RELATED APPLICATIONS

This application is a 371 National Stage of International Application No. PCT/JP2017/029552, filed Aug. 17, 2017, which claims priority to Japanese Application No. JP 2016-161774, filed Aug. 22, 2016, both of which are hereby incorporated by reference in their entireties for all purposes.

FIELD

The present invention relates to a ligand capable of multivalently binding to a glutamine transporter of a cancer cell, in which it is expressed in excess in comparison with a normal cell, and to a composition comprising that ligand.

BACKGROUND

1. Targeting Therapy

Cancer-related diseases have become a serious problem in recent years. According to a report from WHO, 8.2 million people died of cancer-related diseases in 2012, accounting for 13.2% of all deaths. Chemotherapy is one of the methods used to treat cancer. Chemotherapy refers to a treatment method that kills cancer cells by allowing an anticancer drug to circulate in the body. Although chemotherapy offers the advantage of being lowly invasive, the burden placed on the patient's body attributable to adverse side effects is considerable and there are also various restrictions placed on the administration method. Consequently, there is a need to develop anticancer drugs that are able to provide treatment while suppressing adverse side effects while also being able to kill cancer cells, reduce the burden on the patient and improve quality of life (QOL).

Although current chemotherapy typically uses low molecular weight compounds, these compounds also damage normal cells and cause serious adverse side effects. One method for solving this problem is targeting therapy. Targeting therapy refers to modifying a drug with a targeting substance (ligand) that binds to a receptor specifically present only on cancer cells, thereby enabling the drug to be selectively delivered only to cancer tissue with the aim of improving therapeutic efficacy and reducing adverse side effects. At present, low molecular weight substances such as folic acid or hydrocarbons and naturally-occurring compounds such as peptides, proteins, aptamers or antibodies are known to be used as ligands. The advantage of this therapy is that pharmacological effects can be maximized and adverse side effects can be alleviated by combining various types of ligands and drugs, thereby making it possible to use drugs that were previously not applied clinically due to their potent toxicity. One example of a targeting therapy drug consists of antibody-drug conjugates (ADCs) obtained by introducing a drug into an antibody that binds with an antigen specifically present on a cancer cell. Two types of ADCs consisting of trastuzumab emtansine and brentuximab vedotin are currently applied clinically and have been confirmed to reduce adverse side effects and improve therapeutic efficacy (NPL1 and NPL2). In addition, therapeutic drugs that use, for example, folic acid, which targets folate receptors (FR) expressed in excess on cancer cells, as a ligand, are also undergoing clinical trials (NPL3). In this manner, targeting therapy drugs obtained by introducing a drug into a ligand are considered to be extremely useful for improving the pharmacological effects of anticancer drugs.

2. Transporters

As a result of cells becoming malignant, glycolytic pathways are accelerated resulting in the consumption of large amounts of glucose. Consequently, glucose transporters that take up glucose are expressed in excess on the surface of cancer cells resulting in excess uptake of glucose. $^{18}$F-fluorodeoxyglucose-positron emission tomography ([$^{18}$F] FDG-PET), in which a portion of the hydrogen atoms of glucose are converted to $^{18}$F, is used practically for cancer diagnosis by utilizing this increased uptake of glucose in cancer cells (NPL4).

In addition, uptake of amino acids is similarly increased in malignant cells. This is because large amounts of amino acids are required in comparison with normal cells since cancer cells are engaged in rapid growth and protein synthesis. Transporters that take up various amino acids are expressed in excess in cancer cells.

Among these amino acids, glutamine uptake in particular is activated in cancer cells. Uptake of glutamine by cancer cells is known to be accelerated 10-fold to 30-fold in comparison with normal cells. Glutamine is taken up by means of glutamine transporters and catabolized into glutamic acid and α-ketoglutaric acid in cells by enzymes such as glutaminase (GLS), after which it is incorporated into the TCA cycle to produce ATP. Drugs that inhibit the enzyme GLS, which catabolizes glutamine to glutamic acid, demonstrate a certain growth inhibitory effect. In addition, glutamine is also known to be catabolized into asparagine and used in DNA synthesis. Uptake of glutamine is promoted by signaling such as MYC signaling that promotes the glycolytic pathway. The TCA cycle can be maintained due to this action. In this manner, excess uptake of glutamine has a considerable effect on maintaining the cancer environment.

There are various glutamine transporters responsible for transporting glutamine. Glutamine transporters can be broadly divided into Na+-dependent and Na+-independent types, with systems A, N, ASC and B0AT2 belonging to the Na+-dependent type and system L belonging to the Na+-independent type. Among these, ASCT2, belonging to system ASC, is thought to fulfill a significant role in the uptake of glutamine into cancer cells. ASCT2 has high affinity for alanine, serine and cysteine ($K_m$=30 μM to 90 μM) and is involved in the uptake of various amino acids. ASCT2 is particularly involved in the uptake of glutamine and demonstrates especially high affinity for glutamine ($K_m$=20 μM). This is due to chirality of the carbon moiety at the α-position of glutamine (L-type) and the number of carbon atoms between the amino group and carboxy group being one, thereby resulting in the generation of potent electrostatic interaction and hydrogen bonding with ASCT2.

PET probes using glutamine have been developed with the focus on cancer-specific uptake of glutamine, and particularly on the increased uptake of glutamine by ASCT2 (NPL5 and NPL6).

CITATION LIST

Non Patent Literature

[NPL 1] Mallory R. Gordon, et al., Bioconjugate Chem., 2015, 26, 2198-2215
[NPL 2] Enrico Mastrobattista, et al., Advanced Drug Delivery Reviews, 40, 103-127 (1999)

[NPL 3] Nikki Parker, et al., Analytical Biochemistry, 338, 284-293 (2005)
[NPL 4] Ashley M. Groves, et al., Lancet Oncol., 8, 822-830 (2007)
[NPL 5] Zehui Wu, et al., Mol. Pharmaceutics, 11, 3852-3866 (2014)
[NPL 6] Wenchao Qu, et al., J. Am. Chem. Soc., 133, 1122-1133 (2011)

SUMMARY

Technical Problem

Although targeting therapy drugs demonstrate a certain therapeutic effect, they also have several problems. The first problem is the diversity of cancer. For example, folate receptors (FR) are known to have considerably different receptor expression levels depending on the cancer (NPL3). Similarly, in the case of antibodies as well, the type of antigen that is expressed in excess differs according to the type of cancer (NPL2). Consequently, if the type of cancer varies, that cancer cannot be targeted with a single ligand thereby ending up resulting in limitations on treatment.

The second problem is the non-uniformity of cancer. This means that receptors may be expressed at different levels or not expressed at all since the phenotype of each cancer cell varies even within the same cancer tissue. Consequently, cancer cells that do not express receptors cannot be targeted by ligands thereby resulting in the risk of relapse due to the presence of residual cancer cells. In order to solve this problem, it is important to seek out sufficiently expressed receptors regardless of the type of cancer or cell and develop ligands capable of targeting those receptors.

In addition, the third problem is adverse side effects. Ligands currently applied clinically exhibit extremely high binding strength with receptors and are capable of binding to individual receptors, and the expression levels of targeted receptors is also extremely high. However, since these receptors are expressed on the surfaces of normal cells at about ⅓ to ¼ the level of cancer cells, even though adverse side effects are alleviated in comparison with conventional anticancer drugs, these ligands end up causing adverse side effects as a result of also binding to normal cells. In this manner, when conventional methods are used consisting of selecting binding based on the presence or absence of a receptor with a ligand that strongly binds to that receptor, the ligand also ends up binding to normal cells expressing that receptor thereby resulting in the occurrence of adverse side effects. In order to solve this problem, a ligand capable of selecting targeting based on the expression level of a receptor and not on the presence or absence of that receptor is considered to be useful. Such a ligand would not target normal cells having low receptor expression levels but rather would be able to realize targeting of only cancer cells demonstrating high expression levels, thereby making it possible to achieve further alleviation of adverse side effects.

Moreover, in the case of using antibody-drug conjugates, the number of drugs that can be loaded onto an antibody molecule is extremely low at roughly three to four per antibody. In addition, there are also the problems of the difficulty in synthesizing large amounts due to the use of antibodies while also being extremely expensive.

Glutamine is considered to be extremely useful as a novel ligand capable of targeting cancer cells since cancer cells express glutamine transporters in excess and demonstrate increased uptake of glutamine that is 10 times to 30 times greater in comparison with normal cells.

However, in the case of considering the use of glutamine alone as a ligand, the glutamine is predicted to not be able to function as a ligand since binding strength between the glutamine and transporter is weaker than the binding strength typically required by ligand molecules. For example, the value of Michaelis constant $K_m$, which is an indicator of the affinity between ASCT2 and glutamine, is 20 µM. On the other hand, the dissociation constant $K_d$ is used as an indicator of ligand binding strength, and affinity and binding strength are higher the smaller the value of $K_m$ and $K_d$. By definition, although the dissociation constants of ASCT2 and glutamine are thought to adopt a value smaller than 20 µM, which is the aforementioned Michaelis constant, it is unlikely that this value reaches the order of 10 nM, which is typically required by ligands.

Thus, an object of the present invention is to provide a ligand that is capable of selectively targeting all types of cancer.

Solution to Problem

As a result of conducting extensive studies with the foregoing in view, the inventors of the present invention found that, during uptake of glutamine by means of a glucose transporter, a ligand having a plurality of partial structures of glutamine recognized by that transporter is specifically taken up by a cancer cell as a result of multivalently binding to that transporter on the cancer cell, thereby leading to completion of the present invention.

Namely, the present invention has the aspects indicated below.

[1] A ligand capable of multivalently binding to a glutamine transporter that is expressed in excess in a cancer cell as compared with a normal cell, which contains a plurality of groups represented by the following formula (1):

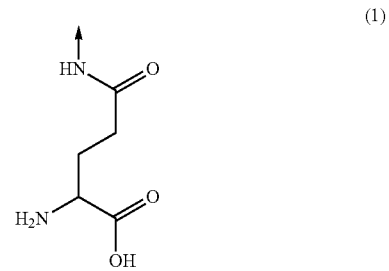

wherein the arrow indicates linkage with another portion of the ligand.

[2] The ligand according to [1], wherein the ligand contains a polymer main chain to which ten or more groups represented by the formula (1) are linked directly or via a linker.

[3] The ligand according to [2], wherein the number average molecular weight of the ligand is 5,000 Da or more.

[4] The ligand according to [2] or [3], wherein the polymer main chain is selected from the group consisting of polyester, polyether, polyacrylate, polypeptide and copolymers thereof.

[5] The ligand according to any of [2] to [4], wherein the polymer main chain is a polypeptide.

[6] The ligand according to [5], wherein a group represented by the following formula (2) is linked to a side chain of ten or more amino acids present in the polypeptide:

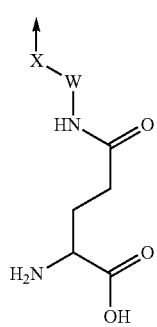

(2)

wherein the arrow indicates linkage to the side chain,

X represents a group selected from the group consisting of —NH—, —O—, —NH—CO—, —C(O)O—, —C(O)S—, —S— and —S—S— or is not present, and W represents a linker selected from the group consisting of a $C_{1-6}$ alkylene group, polyoxyalkylene group and polyaminoalkylene group, or is not present.

[7] The ligand according to [5] or [6], wherein the polypeptide is α-polylysine.

[8] The ligand according to [7], wherein a group represented by the following formula (3) is linked to ten or more side chain amino groups of lysine present in the α-polylysine:

(3)

wherein the arrow indicates linkage to a side chain amino group of lysine.

[9] The ligand according to any of [1] to [8], wherein the terminal primary amino groups of some of a plurality of groups represented by formula (1) are capped with a protective group that is eliminated in a low pH environment.

[10] The ligand according to [9], wherein the protective group that is eliminated in a low pH environment is selected from the group consisting of a phthaloyl group, maleoyl group, 2-carboxybenzoyl group and (2Z)-3-carboxy-2-propenoyl group.

[11] The ligand according to any of [1] to [10], wherein the ligand contains at least one detectable label or anticancer drug.

[12] The ligand according to [11], wherein the detectable label is a fluorescent label, luminescent label, contrast agent, metal atom, compound containing one or more metal atoms, radioisotope, compound containing one or more radioisotopes, nanoparticle or liposome.

[13] The ligand according to [1], wherein the ligand is a compound represented by the following formula (4) or a pharmaceutically acceptable salt thereof:

(4)

wherein n represents an integer of 10 or more.

[14] A composition comprising the ligand according to any of [1] to [13].

[15] A method for diagnosing or detecting cancer comprising the administration of an effective amount of the ligand according to [11] or [12] to a subject in need thereof, wherein the ligand contains at least one detectable label.

[16] The ligand according to [11] or [12] for diagnosing or detecting cancer containing at least one detectable label.

[17] A use of the ligand according to [11] or [12] in the manufacture of a medicament for diagnosing or detecting cancer, wherein the ligand contains at least one detectable label.

[18] A method for treating cancer comprising administration of an effective amount of the ligand according to [11] to a subject in need thereof, wherein the ligand contains at least one anticancer drug.

[19] The ligand according to [11] for treating cancer containing at least one anticancer drug.

[20] A use of the ligand according to [11] in the manufacture of a medicament for treating cancer, wherein the ligand contains at least one anticancer drug.

Advantageous Effects of Invention

Use of the ligand of the present invention makes it possible to selectively target all types of cancer. Conjugating the ligand of the present invention with a drug makes it possible to effectively use the ligand in cancer targeting therapy.

BRIEF DESCRIPTION OF DRAWINGS

FIG. 9 depicts graphs showing the amounts of polymer ligands having different polymerization degrees taken up by Bx-PC3 cells (n=3 each). Polymer ligand concentration: 10 μM, temperature: 37° C.

FIG. 10 depicts graphs showing the amounts of polymer ligands having different polymerization degrees taken up by HepG2 cells (n=3 each). Polymer ligand concentration: 10 μM, temperature: 37° C.

DESCRIPTION OF EMBODIMENTS

Figure 1:
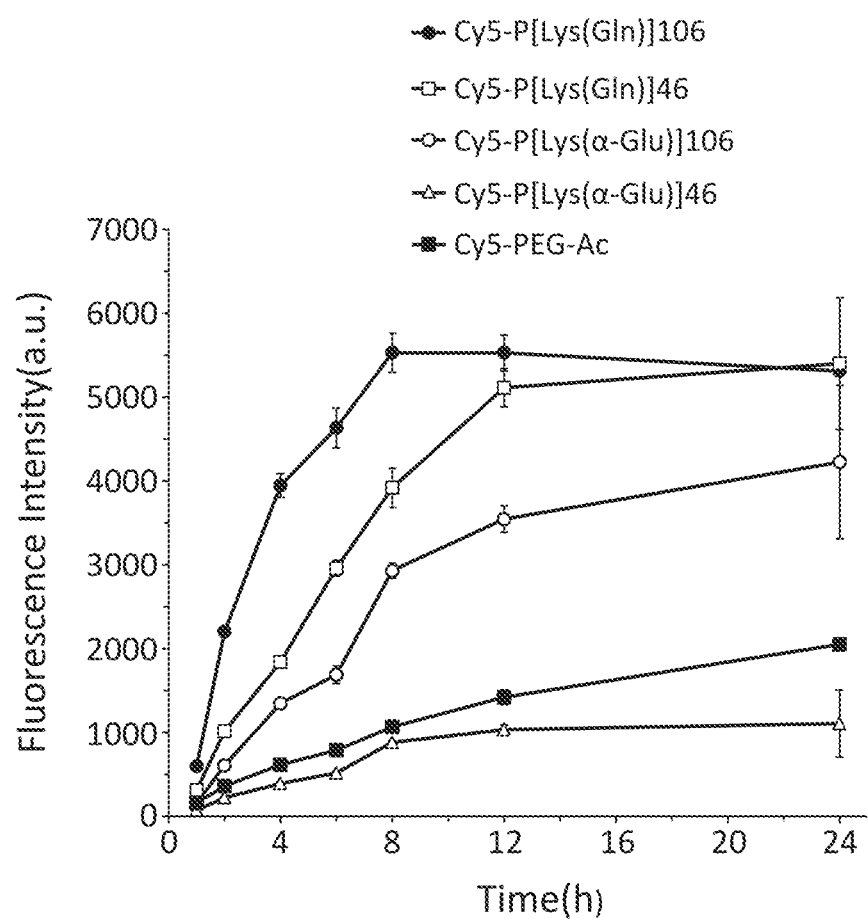
FIG. 1 is a graph showing time-based changes in the amount of ligand taken up by Bx-PC3 cells (n=3), polymer ligand concentration: 10 μM, incubation temperature: 37° C.

One aspect of the present invention relates to a ligand capable of multivalently binding to a glutamine transporter expressed in excess in a cancer cell in comparison with a normal cell, which contains a plurality of groups represented by the following formula (1):

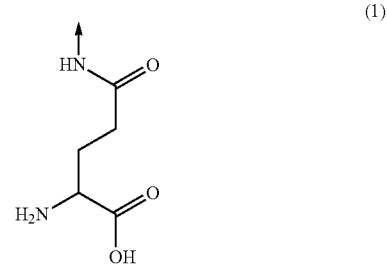

wherein the arrow indicates linkage with another portion of the ligand. This ligand may also be referred to as the "ligand of the present invention".

In the present description, a "ligand" refers to a substance capable of specifically binding to a target site of a cell. There are no particular limitations on the form of the ligand of the present invention, and for example, it may be a molecule containing a plurality of groups represented by formula (1) in a single molecule (also referred to as a "ligand molecule"), or may be a complex of molecules containing at least one group represented by formula (1) in a single molecule (also referred to as a "ligand complex"). There are no particular limitations on the ligand complex and examples thereof include micelles and liposomes having a portion that binds to a target site.

The ligand of the present invention targets a glutamine transporter expressed in excess in a cancer cell in comparison with a normal cell. Here, a "normal cell" refers to a cell of the same type as a targeted cancer cell that has not become malignant. Examples of such glutamine transporters include ASCT2 belonging to system ASC, LAT1 belonging to system L, and SNAT5 belonging to system N. The ligand of the present invention particularly targets ASCT2 of a cancer cell. There are no particular limitations on the degree of excess expression provided expression is greater in comparison with a normal cell. Although varying according to the type of glutamine transporter and type of tissue to which the cancer cell that expresses the transporter belongs, the ligand of the present invention targets a glutamine transporter of a cancer cell that is expressed 1.1 times or more, 1.3 times or more, 1.5 times or more, 2 times or more, 2.5 times or more or 3 times or more in comparison with a normal cell.

In the present description, "multivalent binding" refers to the ligand binding to at least two target sites (namely, glutamine transporters) on a cell by means of a plurality of groups represented by formula (1). Although glutamine alone has extremely low ability to bind to a transporter and is unable to function as a ligand, the ligand of the present invention containing a plurality of glutamines demonstrates considerably increased binding strength to a glutamine transporter in comparison with glutamine alone.

The ligand of the present invention is able to be taken up into a cell by endocytosis after binding to a glutamine transporter.

There are no particular limitations on the stereostructure of groups represented by formula (1) provided the ligand of the present invention is capable of multivalently binding to a glutamine transporter expressed in excess in a cancer cell in comparison with a normal cell, and may have a stereostructure represented by the following formula (1a) or (1b). A group represented by formula (1a), having a stereostructure identical to L-glutamine present in nature, is preferable:

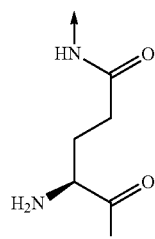

(1a)

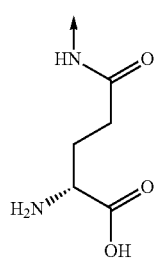

(1b)

wherein the arrow indicates linkage with another portion of the ligand.

There are no particular limitations on the number of groups represented by formula (1) in the ligand of the present invention provided the ligand is capable of multivalently binding to a glutamine transporter expressed in excess in a cancer cell in comparison with a normal cell. The lower limit of the number of these groups is, for example, 10, 15, 20, 25, 30, 35, 40, 45, 50, 60, 70, 80, 90 or 100, while the upper limit of the number of these groups is, for example, 200, 300, 400, 500, 600, 700, 800, 900, 1000, 3000 or 5000. The number of these groups is, for example, 10 to 5000, preferably 10 to 500 and more preferably 20 to 200. The preferable number of these groups varies dependent on the physical structure and chemical characteristics of the substance that binds to these groups.

In one embodiment, the ligand of the present invention contains a polymer main chain to which a plurality of groups represented by formula (1) are linked directly or via a linker. In this case, the number of groups represented by formula (1) is as previously described. The ligand of the present invention preferably contains a polymer main chain to which 10 or more groups represented by formula (1) are linked directly or via a linker. There are no particular limitations on the polymer main chain provided it does not inhibit multivalent binding with a glutamine transporter, and examples thereof include polyurethane, polyester, polyamide, polycarbonate, polyimide, polyether, polyacrylate, polysiloxane, polyvinyl, polypeptide, polynucleotide and copolymers thereof. The polymer main chain is preferably a polyester, polyether, polyacrylate, polypeptide or copolymer thereof. In one embodiment of the present invention, the polymer main chain contains a primary or secondary amino group which can be condensed with a carboxylic acid. In addition, in one embodiment of the present invention, the polymer main chain is a polypeptide. In addition, in one embodiment of the present invention, the polymer main chain is a polypeptide containing a plurality of lysines such as α-polylysine. In the case the ligand of the present invention has a polymer main chain, the lower limit of the number average molecular weight thereof is, for example, 3,000 Da, 4,000 Da, 5,000 Da, 6,000 Da or 7,000 Da (preferably 5,000 Da) and although there are no particular limitations thereon, the upper limit thereof is, for example, 1,500,000 Da, 1,000,000 Da, 500,000 Da, 300,000 Da, 100,000 Da, 70,000 Da or 50,000 Da. In the case the ligand of the present invention has a polymer main chain, the number average molecular weight thereof is preferably 5,000 Da to 150,000 Da and more preferably 6,000 Da to 70,000 Da.

In one embodiment, the polymer main chain of the ligand of the present invention is a polypeptide (such as α-polylysine) and a group represented by the following formula (2) is linked to a plurality of amino acid side chains in the aforementioned polypeptide:

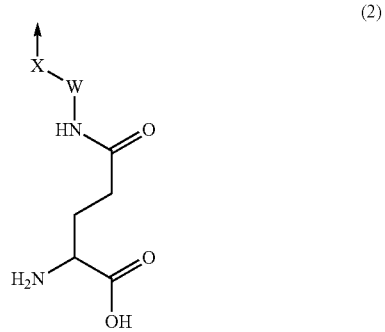

(2)

wherein the arrow indicates linkage to the aforementioned side chain,

X represents a group selected from the group consisting of —NH—, —O—, —NH—CO—, —C(O)O—, —C(O)S—, —S— and —S—S— or is not present, and W represents a linker selected from the group consisting of a $C_{1-6}$ alkylene group, polyoxyalkylene group and polyaminoalkylene group, or is not present. In this case, the number of groups represented by formula (1) is similarly applied to the number of groups represented by formula (2) in the ligand. Preferably, groups represented by the aforementioned formula (2) are linked to 10 or more amino acid side chains present in the aforementioned polypeptide. Preferable combinations of X and W include the case in which X represents —NH— or —NH—CO— and W is a linker, and the case in which X and W are not present.

In the present description, an "alkylene group" refers to a linear or branched alkylene group. In the present description, a "$C_{1-6}$ alkylene group" refers to a linear or branched alkylene group having 1 to 6 carbon atoms, examples of which include a methylene group, ethylene group, propylene group, butylene group, pentylene group, hexylene group and isomers thereof. In the present description, although there are no particular limitations thereon, a "polyoxyalkylene group" refers to, for example, polyoxyethylene, polyoxypropylene, polyoxybutylene or a copolymer thereof. In the present description, although there are no particular limitations thereon, a "polyaminoalkylene group" refers to, for example, polyaminoethylene, polyaminopropylene, polyaminobutylene or s copolymer thereof.

In one embodiment, the polymer main chain of the ligand of the present invention is a polypeptide (such as α-polylysine), and a group represented by formula (1) is linked via a linker to a plurality of side chain amino groups of lysine in the aforementioned polypeptide, or a group represented by the following formula (3) is linked to a side chain amino group of lysine in the polypeptide:

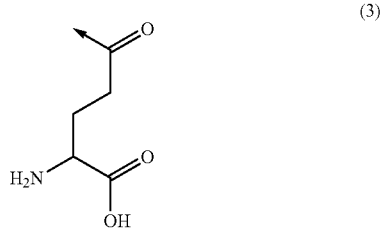

(3)

wherein the arrow indicates linkage to a side chain amino group of lysine. In this case, the number of groups represented by the aforementioned formula (1) is applied to the number of groups represented by formula (3) in the ligand in the same manner. Preferably, groups represented by the aforementioned formula (3) are linked to 10 or more side chain amino groups of lysine present in the aforementioned polypeptide. More preferably, groups represented by the aforementioned formula (3) are linked to all side chain amino groups of lysine present in the aforementioned polypeptide.

In a preferred embodiment, the polymer main chain of the ligand of the present invention is α-polylysine, and a group represented by the following formula (3) is linked to 10 or more (and preferably all) side chain amino groups of lysine present in the aforementioned α-polylysine:

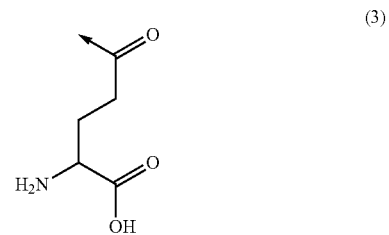

(3)

wherein the arrow indicates linkage to a side chain amino group of lysine.

In the case a group represented by formula (1) is linked to the polymer main chain via a linker, there are no particular limitations on the structure of the linker provided it does not inhibit multivalent binding to a glutamine transporter. For example, the linker is a $C_{1-6}$ alkylene group, polyoxyalkylene group or polyaminoalkylene group, and is preferably a polyoxyethylene group.

In one embodiment, the ligand of the present invention is a polymer micelle comprising a block copolymer containing a hydrophilic polymer segment, in which at least one group represented by formula (1) is linked directly or via a linker, and a hydrophobic polymer segment.

There are no particular limitations on the hydrophilic segment provided it does not inhibit micelle formation, and examples thereof include segments derived from polyalkylene oxides such as polyethylene oxide or polypropylene oxide, polymalic acid, polyaspartic acid, polyglutamic acid, polylysine, polysaccharide, polyacrylamide, polyacrylic acid, polymethacrylamide, polymethacrylic acid, polyvinylpyrrolidone, polyvinyl alcohol, polymethacrylate, polyacrylate, polyamino acid and derivatives thereof.

There are no particular limitations on the hydrophobic segment provided it does not inhibit micelle formation, and examples thereof include poly(β-benzyl-L-aspartate), poly(γ-benzyl-L-glutamate), poly(β-substituted aspartate), poly(γ-substituted glutamate), poly(L-leucine), poly(L-valine), poly(L-phenylalanine), hydrophobic polyamino acids, polystyrene, polymethacrylate, polyacrylate, polymethacrylamide, polyacrylamide, polyamide, polyester, polyalkylene oxide and hydrophobic polyolefins.

Although there are no particular limitations thereon, examples of block copolymers containing a hydrophilic segment and hydrophobic segment include the following: polyethylene oxide-polystyrene block copolymer, polyethylene oxide-polybutadiene block copolymer, polyethylene oxide-polyisoprene block copolymer, polyethylene oxide-polypropylene block copolymer, polyethylene oxide-polyethylene block copolymer, polyethylene oxide-poly(β-benzylaspartate) block copolymer, polyethylene oxide-poly(γ-benzylglutamate) block copolymer, polyethylene oxide-poly(alanine) block copolymer, polyethylene oxide-poly(phenylalanine) block copolymer, polyethylene oxide-poly(leucine) block copolymer, polyethylene oxide-poly(isoleucine) block copolymer, polyethylene oxide-poly(valine) block copolymer, polyacrylic acid-polystyrene block copolymer, polyacrylic acid-polybutadiene block copolymer, polyacrylic acid-polyisoprene block copolymer, polyacrylic acid-polypropylene block copolymer, polyacrylic acid-polyethylene block copolymer, polyacrylic acid poly(β-benzylaspartate) block copolymer, polyacrylic acid-poly(γ-benzylglutamate) block copolymer, polyacrylic acid-poly(alanine) block copolymer, polyacrylic acid-poly(phenylalanine) block copolymer, polyacrylic acid-poly(leucine)

block copolymer, polyacrylic acid-poly(isoleucine) block copolymer, polyacrylic acid-poly(valine) block copolymer, polymethacrylic acid-polystyrene block copolymer, polymethacrylic acid-polybutadiene block copolymer, polymethacrylic acid-polyisoprene block copolymer, polymethacrylic acid-polypropylene block copolymer, polymethacrylic acid-polyethylene block copolymer, polymethacrylic acid-poly(β-benzylaspartate) block copolymer, polymethacrylic acid-poly(γ-benzylglutamate) block copolymer, polymethacrylic acid-poly(alanine) block copolymer, polymethacrylic acid-poly(phenylalanine) block copolymer, polymethacrylic acid-poly(leucine) block copolymer, polymethacrylic acid-poly(isoleucine) block copolymer, polymethacrylic acid-poly(valine) block copolymer, poly(N-vinylpyrrolidone)-polystyrene block copolymer, poly(N-vinylpyrrolidone)-polybutadiene block copolymer, poly(N-vinylpyrrolidone)-polyisoprene block copolymer, poly(N-vinylpyrrolidone)-polypropylene block copolymer, poly(N-vinylpyrrolidone)-polyethylene block copolymer, poly(N-vinylpyrrolidone)-poly(β-benzylaspartate) block copolymer, poly(N-vinylpyrrolidone)-poly(γ-benzylglutamate) block copolymer, poly(N-vinylpyrrolidone)-poly(alanine) block copolymer, poly(N-vinylpyrrolidone)-poly(phenylalanine) block copolymer, poly(N-vinylpyrrolidone)-poly(leucine) block copolymer, poly(N-vinylpyrrolidone)-poly(isoleucine) block copolymer, poly(N-vinylpyrrolidone)-poly(valine) block copolymer, poly(aspartic acid)-polystyrene block copolymer, poly(aspartic acid)-polybutadiene block copolymer, poly(aspartic acid)-polyisoprene block copolymer, poly(aspartic acid)-polypropylene block copolymer, poly(aspartic acid)-polyethylene block copolymer, poly(aspartic acid)-poly(β-benzylaspartate) block copolymer, poly(aspartic acid)-poly(γ-benzylglutamate) block copolymer, poly(aspartic acid)-poly(alanine) block copolymer, poly(aspartic acid)-poly(phenylalanine) block copolymer, poly(aspartic acid)-poly(leucine) block copolymer, poly(aspartic acid)-poly(isoleucine) block copolymer, poly(aspartic acid)-poly(valine) block copolymer, poly(glutamic acid)-polystyrene block copolymer, poly(glutamic acid)-polybutadiene block copolymer, poly(glutamic acid)-polyisoprene block copolymer, poly(glutamic acid)-polypropylene block copolymer, poly(glutamic acid)-polyethylene block copolymer, poly(glutamic acid)-poly(β-benzylaspartate) block copolymer, poly(glutamic acid)-poly(γ-benzylglutamate) block copolymer, poly(glutamic acid)-poly(alanine) block copolymer, poly(glutamic acid)-poly(phenylalanine) block copolymer, poly(glutamic acid)-poly(leucine) block copolymer, poly(glutamic acid)-poly(isoleucine) block copolymer and poly(glutamic acid)-poly(valine) block copolymer.

In the case a group represented by formula (1) is linked to the hydrophilic segment via a linker, there are no particular limitations on the structure of the linker provided it does not inhibit multivalent binding to a glutamine transporter. For example, the linker is a polyoxyalkylene group and preferably a polyoxyethylene group.

The ligand of the present invention may also contain at least one detectable label. In the present description, a "detectable label" refers to an arbitrary atom or compound able to be detected by any existing detection means. There are no particular limitations on the detection means and examples thereof include visual examination, optical examination devices (such as a light microscope, fluorescence microscope, phase-contrast microscope or in vivo imaging device), X-ray devices (such as a simple X-ray device, computed tomography (CT) device, magnetic resonance imaging (MRI) device, nuclear medicine examination device (such as a scintigraphy device or position emission tomography (PET) device) or single photon emission computed tomography (SPECT) device), ultrasound examination devices and thermographic devices. Labels suitable for each detection means are known among persons with ordinary skill in the art and are described in, for example, Lecchi, et al., Q J Nucl. Med. Mol. Imaging, 2007; 51(2): 111-126. There are no particular limitations on the detectable label and examples thereof include fluorescent labels; luminescent labels; contrast agents; metal atoms; compounds containing one or more metal atoms; radioisotopes; compounds containing one or more radioisotopes; nanoparticles; and liposomes.

Examples of labels suitable for detection by visual examination and optical examination devices include various fluorescent labels and luminescent labels. Although there are no particular limitations thereon, specific examples of fluorescent labels that can be used include members of the Cy™ series (such as Cy™ 2, 3, 5, 5.5 or 7), members of the DyLight™ series (such as DyLight™ 405, 488, 549, 594, 633, 649, 680, 750 or 800), members of the Alexa Fluor® series (such as Alexa Fluor® 405, 488, 549, 594, 633, 647, 680 or 750), members of the HiLyte Fluor™ series (such as HiLyte Fluor™ 488, 555, 647, 680 or 750), members of the ATTO series (such as ATTO 488, 550, 633, 647N, 655 or 740), FAM, FITC, Texas Red, GFP, RFP and Qdot.

In addition, although there are no particular limitations thereon, specific examples of luminescent labels that can be used include luminol, luciferin, lucigenin and aequorin.

Examples of labels suitable for detection with X-ray devices include various contrast agents. Although there are no particular limitations thereon, specific examples of contrast agents that can be used include iodine atoms, iodine ions and iodine compounds.

Examples of labels suitable for detection with MRI devices include various metal atoms and compounds containing one or more metal atoms such as complexes containing one or two or more types of these metal atoms. There are no particular limitations thereon and specific examples thereof include gadolinium(III) (Gd(III)), yttrium-88 ($^{88}$Y), indium-111 ($^{111}$In) complexes thereof with a ligand such as diethylenetriamine-pentaacetic acid (DTPA), tetraazacyclodecane-1,4,7,10-tetraacetic acid (DOTA), (1,2-ethanediyldinitrilo)tetraacetic acid (EDTA), ethylenediamine, 2,2'-bipyridine (bipy), 1 10-phenanthroline (phen), 1,2-bis(diphenylphosphine)ethane (DPPE), 2,4-pentanedione (acac) or oxalate salt (ox), superparamagnetic iron oxide (SPIO) and manganese oxide (MnO).

Examples of labels suitable for detection with nuclear medicine examination devices include various radioisotopes and compounds containing one or more radioisotopes such as complexes of one or more radioisotopes. Although there are no particular limitations thereon, examples of radioisotopes that can be used include technetium-99m ($^{99m}$Tc), indium-111 ($^{111}$In), iodine-123 ($^{123}$I), iodine-124 ($^{124}$I), iodine-25 ($^{125}$I), iodine-131 ($^{131}$I), thallium-201 ($^{201}$Tl), carbon-11 ($^{11}$C), nitrogen-13 ($^{13}$C), oxygen-15 ($^{15}$O), fluorine-18 ($^{18}$F), copper-64 ($^{64}$Cu), gallium-67 ($^{67}$Ga), krypton-81m ($^{81m}$Kr), xenon-133 ($^{133}$Xe), strontium-89 ($^{89}$Sr) and yttrium-90 ($^{90}$Y). In addition, although there are no particular limitations thereon, examples of compounds containing radioisotopes include $^{123}$I-IMP, $^{99m}$Tc-HMPAO, $^{99m}$Tc-ECD, $^{99m}$Tc-MDP, $^{99m}$Tc-tetrofosmin, $^{99m}$Tc-MIBI, $^{99m}$TcO$_4$—, $^{99m}$Tc-MAA, $^{99m}$Tc-MAG3, $^{99m}$Tc-DTPA, $^{99m}$Tc-DMSA and $^{18}$F-FDG.

There are no particular limitations on labels suitable for detection with ultrasound examination devices and examples thereof include nanoparticles and liposomes.

For example, in the case the ligand of the present invention contains a polymer main chain, the detectable label may be linked with the polymer main chain either directly or via a linker. In addition, in the case the ligand of the present invention is a polymer micelle, for example, the detectable label may be linked with a block copolymer composing the polymer micelle either directly or via a linker. In addition, a detectable label may be enclosed within the polymer micelle. There are no particular limitations on the type of linker and examples thereof include a $C_{1-6}$ alkylene group, polyoxyalkylene group (including a polyoxyethylene group and the like) and polyaminoalkylene group.

The ligand of the present invention may contain at least one anticancer drug. For example, in the case the ligand of the present invention contains a polymer main chain, the anticancer drug may be linked to the polymer main chain either directly or via a linker. In addition, in the case the ligand of the present invention is a polymer micelle, for example, the anticancer drug may be linked to a block copolymer composing the polymer micelle either directly or via a linker. In addition, the anticancer drug may be enclosed within the polymer micelle. There are no particular limitations on the type of linker and examples thereof include a $C_{1-6}$ alkylene group, polyoxyalkylene group (including a polyoxyethylene group and the like) and polyaminoalkylene group.

Among the plurality of groups represented by formula (1) present in the ligand of the present invention, the terminal primary amino group of at least one (and preferably some) of a plurality of groups may be capped with a protective group that is eliminated in a low pH environment. The aforementioned protective group may also be hereinafter referred to as a "capping group". The pH in the vicinity of cancer tissue (6.5 to 6.8) is known to be lower in comparison with the pH in the vicinity of normal tissue (about 7.4). For example, by linking a capping group that is not removed at the pH in the vicinity of normal tissue but is removed at the pH in the vicinity of cancer tissue to the terminal primary amino group of a group represented by formula (1), a ligand can be obtained in which the glutamine transporter recognition site is exposed only in cancer tissue. As a result, specificity of the ligand for cancer cells can be improved. Although there are no particular limitations on the aforementioned capping group provided it is eliminated in a low pH environment, examples thereof include protective groups that are eliminated at a pH of 6.8 or lower such as a phthaloyl group, maleoyl group, 2-carboxybenzoyl group or (2Z)-3-carboxy-2-propenoyl group.

In one embodiment of the present invention, the ligand of the present invention is a compound represented by the following formula (4) or a pharmaceutically acceptable salt thereof:

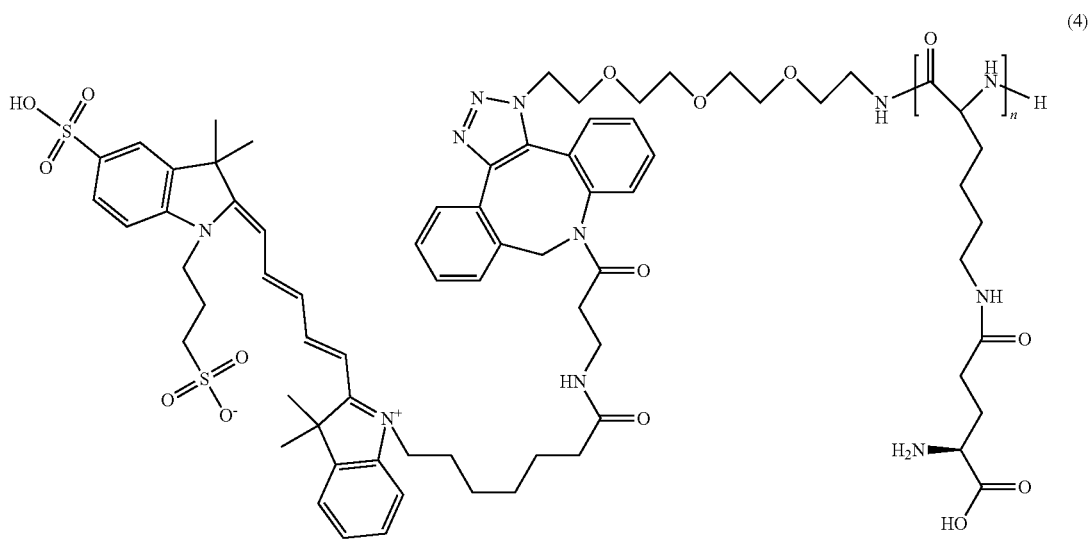

(4)

wherein n represents an integer of 10 or more. n represents polymerization degrees and although the lower limit thereof is 10, it is preferably 15, 20, 25, 30, 35, 40, 45, 50, 60, 70, 80, 90 or 100. Although there are no particular limitations on the upper limit of n, it is, for example, an integer of 200, 300, 400, 500, 600, 700, 800, 900, 1000, 3000 or 5000. n is, for example, an integer of 10 to 5000, is preferably an integer of 10 to 500, and is more preferably an integer of 20 to 200. The aforementioned polymerization degrees can be calculated by the end-group determination method based on integrated values of the $^1$H-NMR spectrum.

In the present description, a "pharmaceutically acceptable salt" refers to a salt of a free form compound that is Although there are no particular limitations thereon, examples of anticancer drugs able to be used in the ligand of the present invention include adriamycin, paclitaxel, docetaxel, cisplatin, mitomycin-C, daunomycin, fluorouracil (5-FU), gemcitabine hydrochloride, emtansine, calichemicin, toxins (such as cytotoxins such as Diphtheria toxin or *Pseudomonas aeruginosa* exotoxin), boron-containing pharmaceuticals (such as bortezomib or drugs such as p-boronophenylalanine able to be used in boron neutron capture therapy (BNCT), nucleic acid pharmaceuticals (such as decoy nucleic acids, antisense nucleic acids, siRNA, miRNA, ribozymes or aptamers), and photosensitizers able to be used in photodynamic therapy (PDT) (such as porphyrin derivatives).

pharmaceutically acceptable and has a desired pharmacological activity. There are no particular limitations on the "pharmaceutically acceptable salt" and examples thereof include salts of inorganic acids such as sulfuric acid, hydrochloric acid, hydrobromic acid, phosphoric acid or nitric acid, salts of organic acids such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid or naphthalene-2-sulfonic acid, salts of one type or a plurality of metal ions such as lithium ions, sodium ions, potassium ions, calcium ions, magnesium ions, zinc ions or aluminum ions, and salts of amines such as ammonia, arginine, lysine, piperazine, choline, diethylamine, 4-phenylcyclohexylamine, 2-aminoethanol and benzathine.

The ligand of the present invention can be produced by introducing a plurality of groups represented by formula (1) into a molecule or complex using various known methods. For example, in the case the ligand of the present invention contains a polymer main chain and the polymer main chain contains a primary or secondary amino group capable of bonding with a carboxylic acid (such as in the case the polymer main chain is a polypeptide containing a plurality of amino acids having amino groups in a side chain in the manner of lysine), the ligand of the present invention may be produced by condensing a compound represented by the following formula (5) into the polymer main chain under known condensation conditions followed by removing the protective group:

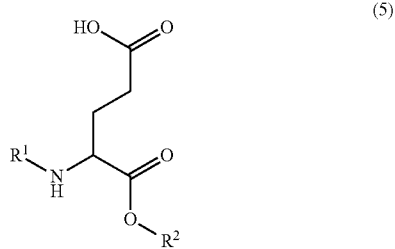

(5)

wherein $R^1$ represents a protective group of an amino group (such as a Boc group) and $R^2$ represents a protective group of a carboxylic acid (such as a benzyl group). Suitable protective groups and deprotection conditions thereof, such as those described in T. W. Greene, Protective Groups in Organic Synthesis, Wiley, New York, 1999, can be used. In addition, in the case the ligand of the present invention is a polymer micelle comprising a block copolymer containing a hydrophilic polymer segment and a hydrophobic polymer segment and a primary or secondary amino group capable of bonding with a carboxyl acid is present in the hydrophilic polymer segment, a group represented by formula (1) can be introduced into the hydrophilic polymer segment by applying a method similar to that described above.

In addition, in the case the ligand of the present invention is a polymer micelle comprising a block copolymer containing a hydrophilic polymer segment and a hydrophobic polymer segment, there are no particular limitations on the method used to form the micelle provided it allows the formation of a polymer micelle. For example, a polymer micelle can be prepared by dissolving or dispersing a block copolymer in an aqueous medium followed by stirring. At that time, physical energy in the form of ultrasonic waves, pressure, shear force or a combination thereof may be imparted. In addition, a polymer micelle can be prepared by dissolving the block copolymer in a volatile organic solvent followed by volatizing the organic solvent and drying to a solid, adding an aqueous medium thereto and stirring, and applying physical energy in the form of ultrasonic waves, pressure, shear force or a combination thereof, or adding an aqueous medium to the block copolymer and applying physical energy in the manner described above. Here, examples of a volatile organic solvent include methanol, ethanol, acetone, chloroform, acetonitrile, tetrahydrofuran and dichloromethane. Here, examples of an aqueous medium include water, physiological saline and buffer solutions, and may contain a small amount of organic solvent provided it does not have an effect on formation of the polymer micelle.

One aspect of the present invention relates to a composition comprising the ligand of the present invention. This composition is also hereinafter referred to as the "composition of the present invention". The composition of the present invention may further comprise a pharmaceutically acceptable carrier, diluent, buffering agent, vehicle or combination thereof. For example, in the case the ligand of the present invention contains a detectable label, the composition of the present invention can be used as a composition for diagnosing or detecting cancer. In addition, in the case the ligand of the present invention contains an anticancer drug, for example, the composition of the present invention can be used as a composition for the treatment of cancer. In the case the composition of the present invention is administered to the body, although there are no particular limitations on the administration route, examples thereof include intravenous administration, subcutaneous administration, intramuscular administration, intraarticular administration, intraperitoneal administration and intraocular administration. In addition, the dosage is suitably selected according to such factors as type of disease and subject age, body weight or gender.

In the present description, a "subject" refers to any mammal. Although there are no particular limitations thereon, examples of the "subject" include humans, primates, mice, rats, dogs, cats, cows, horses, pigs, sheep, goats and camels.

One aspect of the present invention relates to a method for diagnosing or detecting cancer that includes administration of an effective amount of the ligand of the present invention to a subject in need thereof, wherein the aforementioned ligand contains at least one detectable label.

One aspect of the present invention relates to the ligand of the present invention for diagnosing or detecting cancer, wherein the aforementioned ligand contains at least one detectable label.

One aspect of the present invention relates to a use of the ligand of the present invention in the manufacture of a medicament for diagnosing or detecting cancer, wherein the aforementioned ligand contains at least one detectable label.

One aspect of the present invention relates to a method for treating cancer that includes administration of an effective amount of the ligand of the present invention to a subject in need thereof, wherein the aforementioned ligand contains at least one anticancer drug.

One aspect of the present invention relates to the ligand of the present invention for treating cancer, which contains at least one anticancer drug.

One aspect of the present invention relates to a use of the ligand of the present invention in the manufacture of a medicament for treating cancer, wherein the aforementioned ligand contains at least one anticancer drug.

EXAMPLES

Although the following provides a more detailed explanation of the present invention by referring to the following examples and comparative examples, it goes without saying that the scope of the invention is not limited by the examples.

<Reagents>
N-ε-trifluoroacetyl-L-lysine-N-carboxyanhydride (Lys(TFA)-NCA): Chuo Kasei
11-azido-3,6,9-trioxaundecan-1-amine: Sigma Aldrich
Dimethylsulfoxide (DMSO): Kanto Chemical
Boc-Glu-OBzl: Sigma Aldrich
Boc-Glu(OBzl)-OH: Sigma Aldrich
4-(4,6-dimethoxy-1,3,5-triazin-2-yl)-4-methyl morpholinium chloride (DMT-MM): Fluorochem
Triethylamine (TEA): Kanto Chemical
5N HCl: Wako Pure Chemical Industries
Methanol: Kanto Chemical
5N NaOH: Wako Pure Chemical Industries
Acetic acid (AcOH): Wako Pure Chemical Industries
Cy5-DBCO: Click Chemistry Tools
NaHCO$_3$: Wako Pure Chemical Industries
NaCl: Vetec
N-methylpyrrolidone (NMP): Kanto Chemical
Lithium bromide (LiBr): Sigma Aldrich
D-PBS(−) (PBS): Wako Pure Chemical Industries
Trypsin-EDTA solution (Trp): Sigma Aldrich
Dulbecco's modified Eagle's medium (DMEM)
Roswell Park Memorial Institute medium (RPMI)
Fetal bovine serum (FBS): Thermo Scientific
Penicillin-Streptomycin (PS): Sigma Aldrich
EGM™-2 Bullet Kit™: Lonza
O-benzyl-L-serine (Bzl-Ser): Tokyo Chemical Industry
L-glutamine (Gln): Wako Pure Chemical Industries
Anti-ASCT2 antibody (H-52): Santa Cruz
Goat anti-rabbit IgG H & L (DyLight® 488): Abcam
Bovine serum albumin (BSA)
Hoechst 33342: Thermo Scientific
p-Formaldehyde: Wako Pure Chemical Industries
Tris-buffered saline (TBS): Sigma
Tween20: Bethyl
VectaShield mounting medium (VectaShield): Vector
Acetal-PEG-NH$_2$ (Mw: 10 kDA): NOF
Acetic anhydride: Wako Pure Chemical Industries
Cy5-NH$_2$: Thermo Fisher Scientific
N,N-dimethylformamide (DMF): Kanto Chemical
2-picoline borane (Pic-BH$_3$): Wako Pure Chemical Industries
Passive lysis buffer: Promega
Heparin: Wako Pure Chemical Industries <Cell Types and Animals>
Bx-PC3 cells (human pancreatic cancer cell line)
HepG2 cells (human hepatoma cell line)
HUVEC cells (human umbilical vein endothelial cell line)
BALB/c-nu/nu nude mice (female): Oriental Yeast <Measuring Instruments and Analytical Software>
NMR: Bruker 400 MHz
Gel permeation chromatography (GPC): Jasco (column: Superdex 200 Increase, detector: UV 220 nm)
Fluorescence spectrophotometer (FP8300): Jasco
Guava Easy Cyte6-2L: Merck, excitation wavelength: 642 nm, absorption wavelength: 661 nm
Confocal laser scanning microscope (LSM710): Zeiss
Fluorescence spectrophotometer (FP8300): Jasco
IVIS Imaging System: PerkinElmer, excitation wavelength: 640 nm, measurement absorption wavelength: 700 nm
ZEN2012: Zeiss
Imalis: Zeiss <Abbreviations>
Compounds represented by the following formula (4) are hereinafter also referred to as "Cy5-P[Lys(Gln)]n". These compounds employ a structure in which amino groups of the side chains of polylysine have been condensed with the carboxyl groups at the γ-position of glutamic acids. In addition, a fluorescent dye in the form of Cy5 is linked to the end of polylysine via a linker.

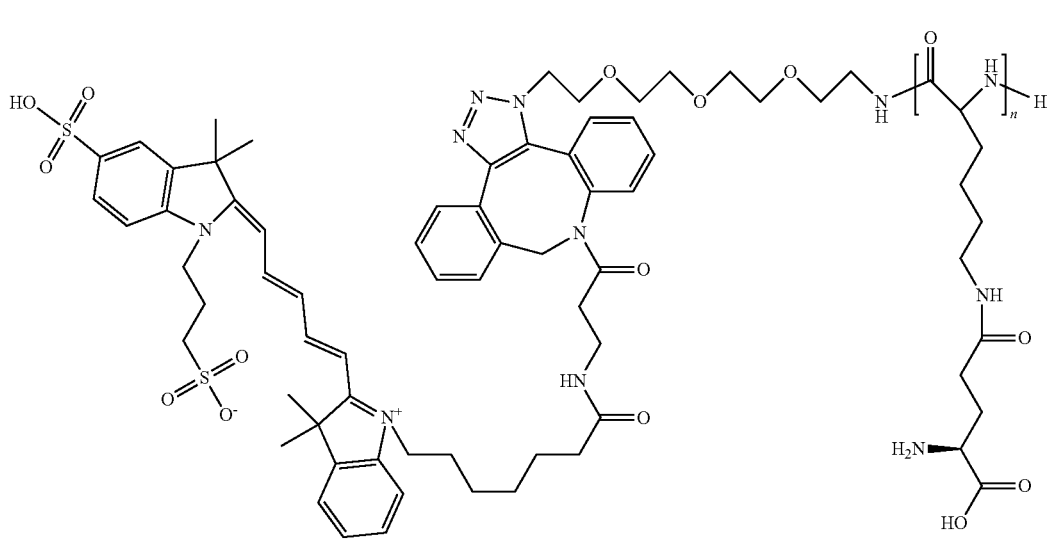

(4)

Here, that in which n=25 is referred to as "Cy5-P[Lys(Gln)]25", that in which n=46 is referred to as "Cy5-P[Lys(Gln)]46", and that in which n=106 is referred to as "Cy5-P[Lys(Gln)] 106".

Compounds represented by the following formula (6) are hereinafter also referred to as "Cy5-P[Lys(α-Glu)]n". The difference between these compounds and those referred to as Cy5-P[Lys(Gln)n" is that these compounds employ a structure in which amino groups of the side chains of polylysine have been condensed with the carboxyl group at the α-position of glutamic acid.

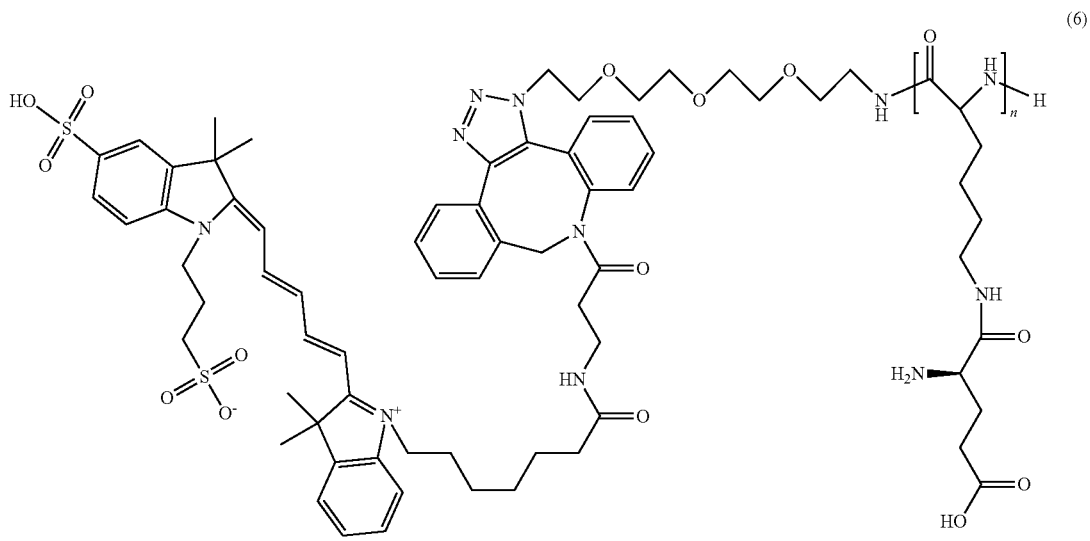

(6)

Here, that in which n=46 is referred to as "Cy5-P[Lys(α-Glu)]46" and that in which n=106 is referred to as "Cy5-P[Lys(α-Glu)]106".

A medium obtained by mixing 50 ml of FBS and 5 ml of penicillin-streptomycin (PS) with 500 ml of DMEM is hereinafter simply referred to as "DMEM medium". In addition, a medium obtained by mixing 50 ml of FBS and 5 ml of PS with 500 ml of RPMI is hereinafter simply referred to as "DMEM medium". A medium obtained by mixing 50 ml of FBS with 500 ml of PBS is referred to as "PBS+10% FBS".

Example 1

Synthesis of Cy5-P[Lys(Gln)n (n=25, 46, 106)
(1) Synthesis of Compound (b) (n=25, 46, 106)

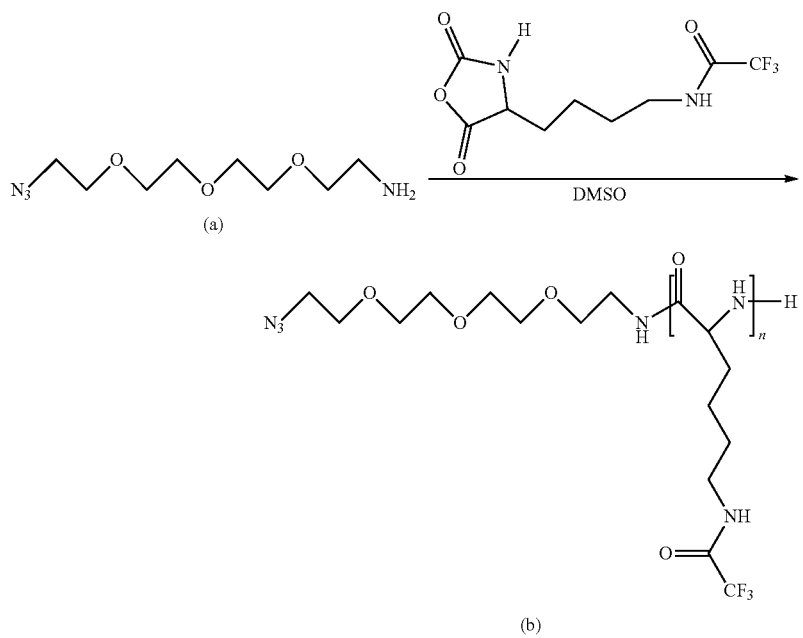

In the case n=106, 2 g of Lys(TFA)-NCA (100 equivalents with respect to 11-azido-3,6,9-trioxaundecan-1-amine) were placed in a flask, in which the air inside had been replaced with Ar, and dissolved in 20 ml of distilled DMSO. 16 μl of 11-azido-3,6,9-trioxaundecan-1-amine were added followed by stirring for 3 days at room temperature. Following completion of the reaction, the reaction solution was dialyzed (MWCO: 6 kDa to 8 kDa) four times using methanol followed by drying under reduced pressure to recover Compound (b) (n=106). In the case n=46 or n=25, Compound (b) (n=25, 46) was obtained in the same manner as described above with the exception of adding 32 μl or 64 μl, respectively, of 11-azido-3,6,9-trioxaundecan-1-amine. The yield was about 75% in all cases.

(2) Synthesis of Compound (c) (n=25, 46, 106)

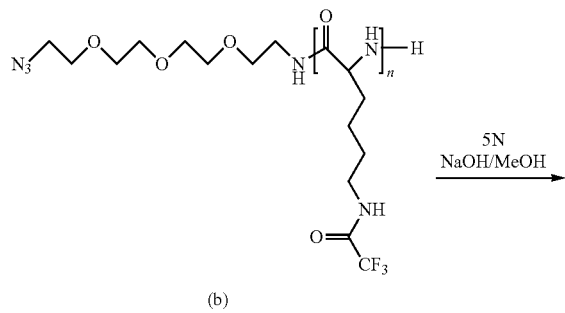

(b)

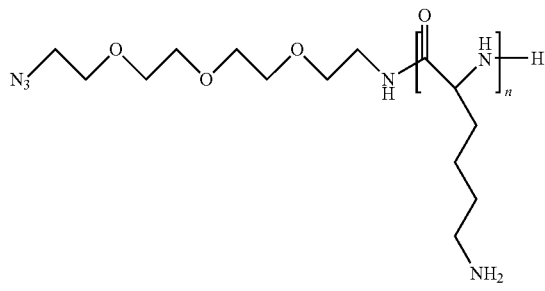

(c)

Compound (b) (n=25, 46, 106) was dissolved in 25 ml of 5N NaOH aq/MeOH (¼ (vol)) and stirred for 8 hours followed by dialysis (MWCO: 6 kDA to 8 kDa, twice with dilute aqueous hydrochloric acid→twice with pure water). Subsequently, the reaction solution was freeze-dried to recover Compound (c) (n=25, 46, 106). The yield was about 80% in all cases.

(3) Synthesis of Compound (d) (n=25, 46, 106)

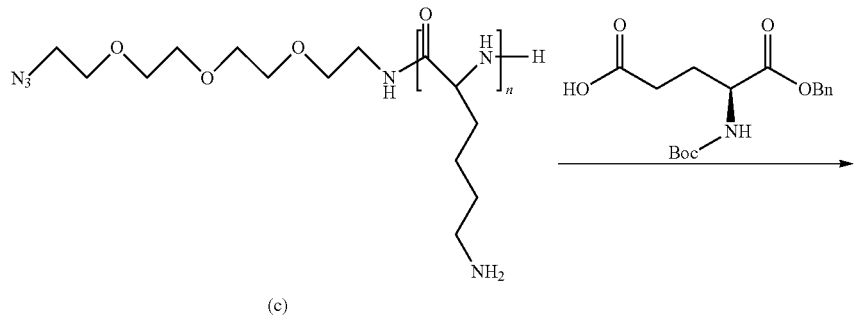

(c)

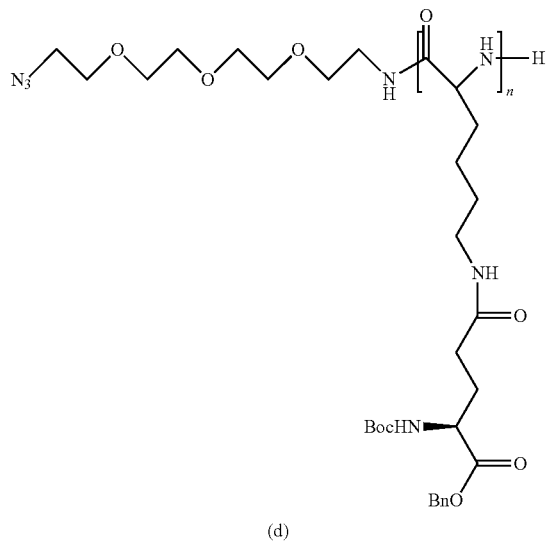

(d)

100 mg (1 Eq) of Compound (c) (n=25, 46, 106), 360 mg (n×1.5 Eq) of Boc-Glu-OBzl and 325 mg (n×1.5 Eq) of DMT-MM were dissolved in DMSO/TEA (10/1 (vol)) and stirred for 1 day at normal temperature. The reaction solution was dialyzed (MWCO: 6 kDa to 8 kDa) four times in MeOH and the solvent was distilled off with an evaporator followed by drying under reduced pressure to recover Compound (d) (n=25, 46, 106). The yield was about 70% in all cases.

(4) Synthesis of Compound (e) (n=25, 46, 106)

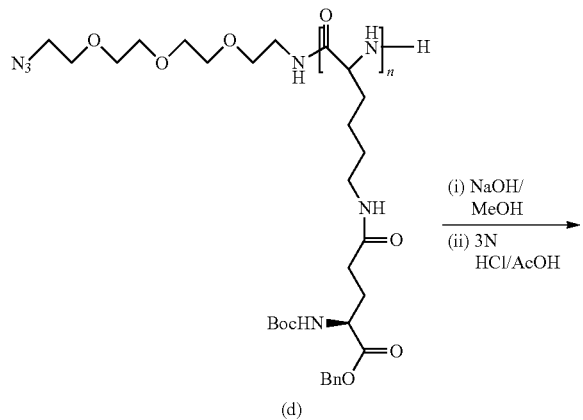

(d)

(i) NaOH/MeOH
(ii) 3N HCl/AcOH

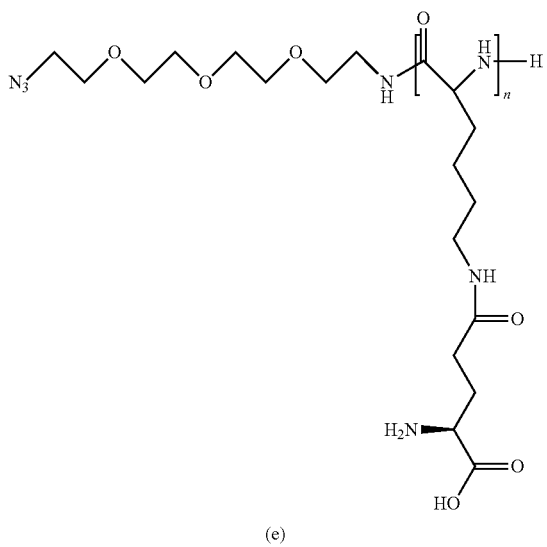

(e)

Compound (d) (n=25, 46, 106) was dissolved in 10 ml of 1 N NaOH/MeOH (1/1 (vol)) and stirred for 18 hours at normal temperature. After stirring, the reaction solution was dialyzed (MWCO: 6 kDa to 8 kDa) four times using MeOH and the solvent was distilled off with an evaporator followed by drying under reduced pressure to recover the debenzylated form. The yield was about 85% in all cases.

Figure 17:
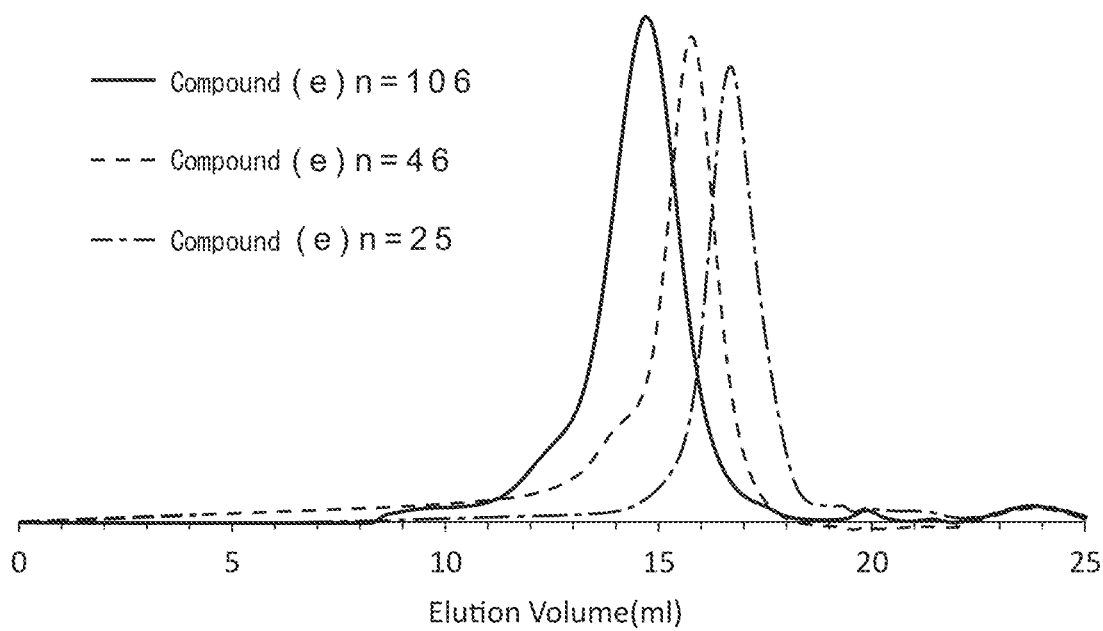
FIG. 17 indicates the GPC spectra of Compound (e) of Example 1 (n=25, 46, 106). (Eluent: 10 mM PB, 140 mM NaCl, pH: 7.4, flow rate: 0.75 ml/min, detector: UV 220 nm)

The aforementioned debenzylated form was dissolved in 15 ml of 3N HCl/AcOH (1/1 (vol)) and stirred for 18 hours at normal temperature. After stirring, the reaction solution was dialyzed (MWCO: 6 kDa to 8 kDa) four times using pure water followed by removing the water by freeze-drying to recover Compound (e) (n=25, 46, 106). The yield was about 85% in all cases. The GPC spectra of the resulting Compound (e) (n=25, 46, 106) are shown in FIG. 17.

Compound (e) (n=25)

$^1$H NMR (400 MHz, $D_2O$): δ (ppm)=1.3-1.9 (150H, —$CH_2CH_2CH_2CH_2$NHCO—), 2.1-2.4 (100H, —NHCO$CH_2CH_2$CH(COOH)$NH_2$), 3.1 (50H, —$CH_2$CH$_2$CH$_2$CH$_2$NHCO—), 3.4-3.7 (16H, —$CH_2CH_2$O— of initiator), 3.8 (25H, —NHCO$CH_2$CH$_2$CH(COOH)$NH_2$), 4.1 (25H, —COCHNH—)

Compound (e) (n=46)

$^1$H NMR (400 MHz, $D_2O$): δ (ppm)=1.3-1.9 (276H, —$CH_2CH_2CH_2CH_2$NHCO—), 2.1-2.4 (184H, —NHCO$CH_2CH_2$CH(COOH)$NH_2$), 3.1 (92H, —$CH_2CH_2CH_2CH_2$NHCO—), 3.4-3.7 (16H, —$CH_2CH_2$— of initiator), 3.8 (46H, —NHCO$CH_2$CH$_2$CH(COOH)$NH_2$), 4.1 (46H, —COCHNH—)

Compound (e) (n=106)

$^1$H NMR (400 MHz, $D_2O$): δ (ppm)=1.3-1.9 (636H, —$CH_2CH_2CH_2CH_2$NHCO—), 2.1-2.4 (424H, —NHCO$CH_2CH_2$CH(COOH)$NH_2$), 3.1 (212H, —$CH_2CH_2CH_2CH_2$NHCO—), 3.4-3.7 (16H, —$CH_2CH_2$O— of initiators), 3.8 (106H, —NHCO$CH_2$CH$_2$CH(COOH)$NH_2$), 4.1 (106H, —COCHNH—)

(5) Synthesis of Cy5-P[Lys(Gln)]n (n=25, 46, 106)

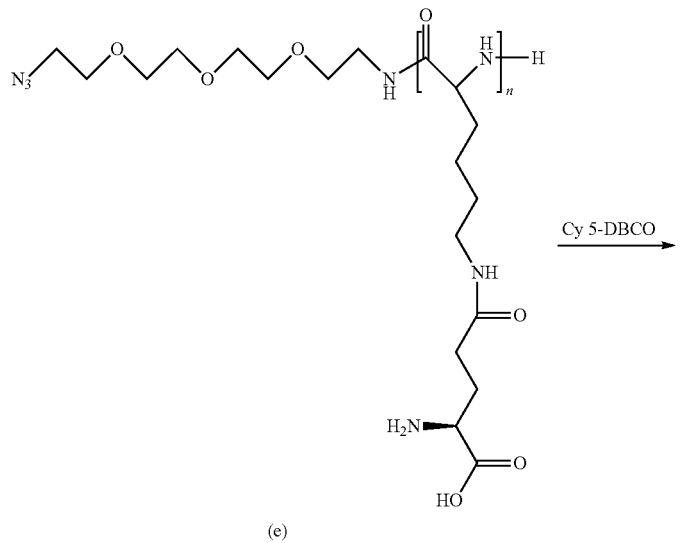

(e)

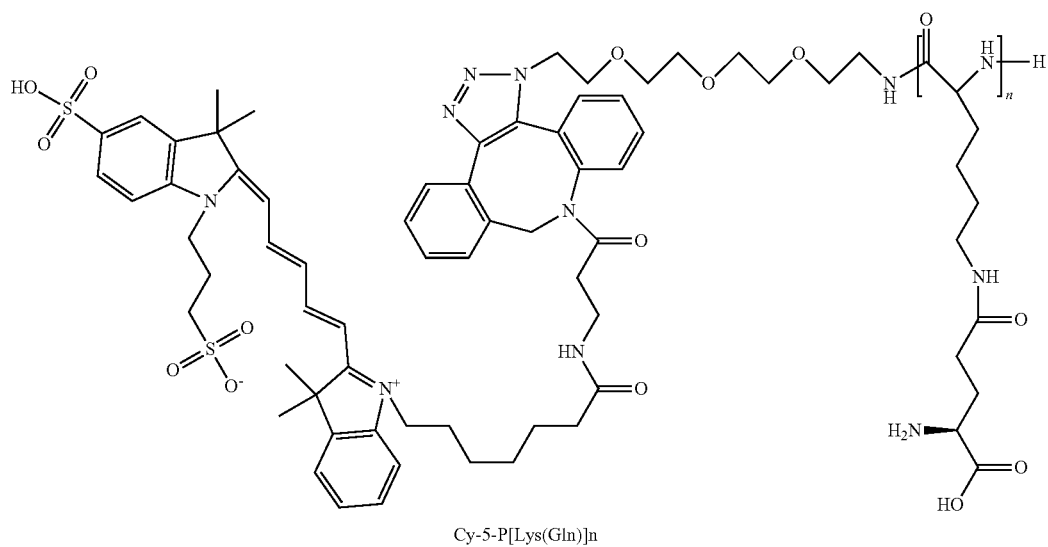

Cy-5-P[Lys(Gln)]n

Compound (e) (n=25, 46, 106) (1.7 Eq) and 200 μl (1 Eq) of Cy5-DBCO/DMSO (5 mg/ml) were dissolved in 10 ml of 10 mM NaHCO$_3$ and 1 M NaCl (pH 7.4) and stirred overnight at normal temperature. After stirring, the reaction solution was dialyzed (MWCO: 6 kDa to 8 kDa) four times using pure water followed by freeze-drying. Subsequently, after removing unreacted Cy5-DBCO with a PC-10 column (solvent: 1 M NaCl), the reaction solution was dialyzed (MWCO: 6 kDa to 8 kDa) three times in water. Finally, the dialyzed reaction solution was freeze-dried to recover Cy5-

Figure 18:
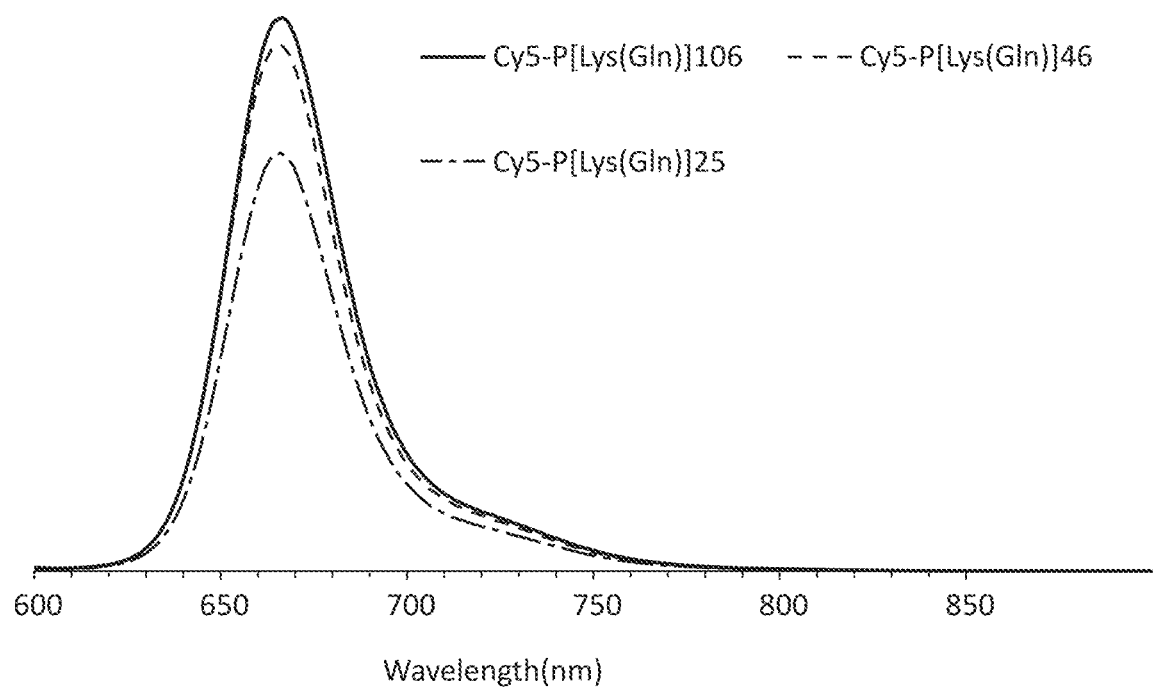
FIG. 18 indicates the fluorescence spectra of Cy5-P[Lys(Gln)]n (n=25, 46, 106). Excitation wavelength: 550 nm FIG. 19 indicates the fluorescence spectra of Cy5-P[Lys(α-Glu)]n (n=46, 106). Excitation wavelength: 550 nm

P[Lys(Gln)]n (n=25, 46, 106). The yield was about 65% in all cases. The fluorescence spectra of the resulting compound are shown in FIG. 18.

Comparative Example 1

Synthesis of Cy5-P[Lys(α-Glu)]n (n=46, 106)
(1) Synthesis of Compound (f) (n=46, 106)

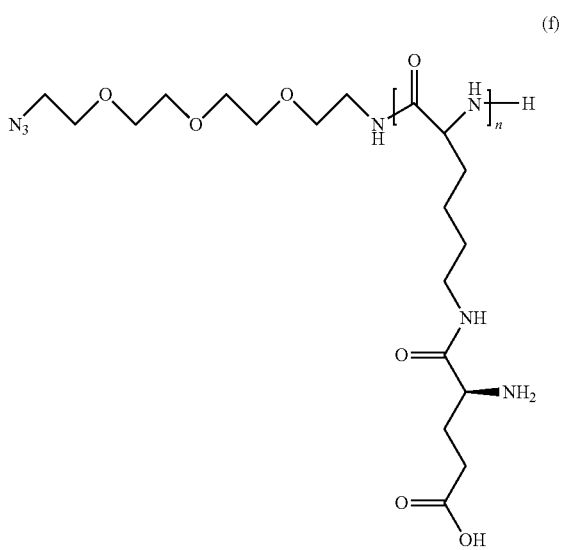

(f)

Compound (f) was prepared according to the same method as in sections (3) and (4) of Example 1 using Boc-Glu(OBzl)-OH instead of Boc-Glu-OBzl.

Compound (f) (n=46)
$^1$H NMR (400 MHz, D$_2$O): δ (ppm)=1.3-1.9 (276H, —CH$_2$CH$_2$CH$_2$CH$_2$NHCO—), 2.1-2.4 (184H, —NHCOCH(NH$_2$)CH$_2$CH$_2$COOH), 3.1-3.3 (92H, —CH$_2$CH$_2$CH$_2$CH$_2$NHCO—), 3.4-3.7 (16H, —CH$_2$CH$_2$O— of initiator), 4.0 (46H, —NHCOCH(NH$_2$)CH$_2$CH$_2$COOH), 4.1 (46H, —COCHNH—)

Compound (f) (n=106)
$^1$H NMR (400 MHz, D$_2$O): δ (ppm)=1.3-1.9 (636H, —CH$_2$CH$_2$CH$_2$CH$_2$NHCO—), 2.1-2.4 (424H, —NHCOCH(NH$_2$)CH$_2$CH$_2$COOH), 3.1-3.3 (212H, —CH$_2$CH$_2$CH$_2$CH$_2$NHCO—), 3.4-3.7 (16H, —CH$_2$CH$_2$O— of initiator), 4.0 (106H, —NHCOCH(NH$_2$)CH$_2$CH$_2$COOH), 4.1 (106H, —COCHNH—)

(2) Synthesis of Cy5-P[Lys(α-Glu)]n (n=46, 106)

Figure 19:
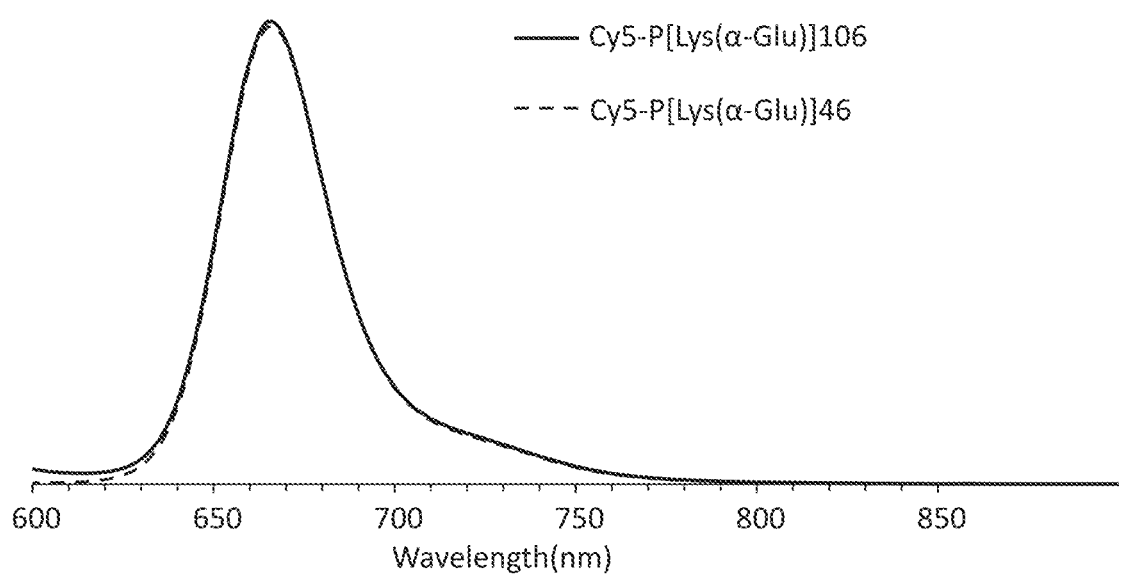

Cy5-P[Lys(α-Glu)]n (n=46, 106) was prepared according to the same method as in section (5) of Example 1 using Compound (f) (n=46, 106). The fluorescence spectra of the resulting compounds are shown in FIG. 19.

Comparative Example 2

Synthesis of Cy5-PEG-Ac

Acetal-PEG-NH$_2$ (Mw: 10 kDa) was reacted with acetic anhydride in DMF to protect the amino groups with acetyl groups. Subsequently, the acetal groups were deprotected in 0.1 N HCl to obtain aldehyde groups. Subsequently, this polymer, Cy5-NH$_2$ and a reducing agent in the form of Pic-BH$_3$ were reacted in MeOH/acetic acid (10/1 (vol)) to introduce Cy5 by reductive amination and prepare Cy5-PEG-Ac.

Example 2

Changes in Intracellular Uptake During Contact of Prescribed Duration with Ligand In order to evaluate whether or not the compounds synthesized in Example 1 demonstrate the function of a ligand, changes in uptake when a cancer cell line (BxPC-3 cells), in which a glutamine transporter in the form of ASCT2 is expressed in excess, was contacted for a prescribed amount of time with the compounds of Example 1 and Comparative Examples 1 and 2 were evaluated based on intracellular fluorescence intensity as determined by flow cytometry.

Bx-PC3 cells were suspended in RPMI medium to prepare a cell suspension containing 1.25×10$^5$ cells/ml. 400 μl aliquots of this cell suspension were seeded into the wells of a 24-well plate (5.0×10$^4$ cells per well) and incubated for 24 hours at 37° C. After removing the medium and washing once with PBS, 400 μl of the Cy5-P[Lys(Gln)46 and Cy5-P[Lys(Gln)106 synthesized in Example 1, Cy5-P[Lys(α-Glu)]46 and Cy5-P[Lys(α-Glu)]106 synthesized in Comparative Example 1 and Cy5-PEG-Ac were added at a concentration of 10 μM and incubated for 1, 2, 4, 6, 8, 12 or 24 hours at 37° C. After incubating for the prescribed time, the solvent was removed followed by washing twice with PBS, and after adding 150 μl of Trp and incubating for 7 minutes at 37° C., 150 μl of PBS+10% FBS were added followed by measurement with a flow cytometer (FCM).

The changes in uptake when contacted with each polymer ligand for a prescribed amount of time are shown in FIG. 1. Uptake was confirmed to have reached a constant level after 8 hours in the case of Cy5-P[Lys(Gln)]106 and after 12 hours in the case of Cy5-P[Lys(Gln)]46. This is thought to be the result of Cy5-P[Lys(Gln)]106 being taken up more easily due to its greater binding strength to cells in comparison with Cy5-P[Lys(Gln)]46, thereby enabling uptake of Cy5-P[Lys(Gln)]106 to have reached saturation in a shorter amount of time. On the other hand, although uptake continued to increase up to 24 hours in the cases of Cy5-P[Lys (α-Glu)]46 and Cy5-P[Lys(α-Glu)]106, this is thought to be due to weak binding strength with cells, thereby preventing uptake from reaching saturation in 24 hours.

Example 3

Evaluation of Intracellular Uptake for Different Cell Types

ASCT2, which is the target of Cy5-P[Lys(Gln)]n, is expressed in excess in various cancer cells, and has been reported to be expressed in excess in pancreatic cancer cells and hepatoma cells in particular. Although evaluation of the ligand function of Cy5-P[Lys(Gln)]n in pancreatic cancer cells (Bx-PC3 cells) was confirmed in Example 2, in order to confirm whether or not ligand function is similarly demonstrated in hepatoma cells and to confirm whether or not there is a difference in uptake between cancer cells and normal cells, ligand uptake was evaluated using Bx-PC3 (pancreatic cancer cells), HepG2 (hepatoma cells) and HUVEC (normal cells).

Figure 2:
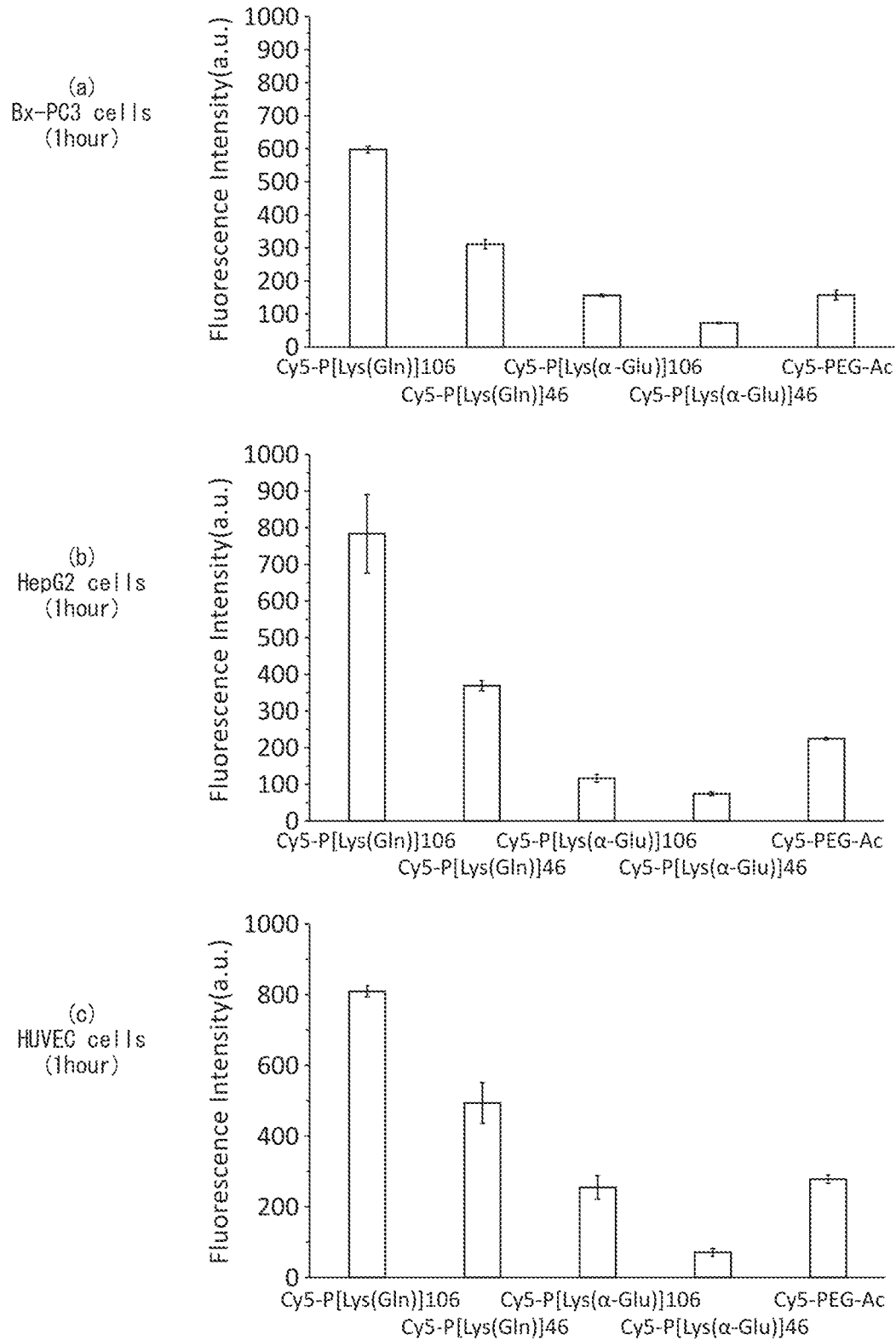
FIG. 2 depicts graphs showing a comparison of the amounts of polymer ligands taken up by cells in the case of incubating for 1 hours (n=3 each). (a) Bx-PC3 cells, (b) HepG2 cells, (c) HUVEC cells, polymer ligand concentration: 10 μM, incubation temperature: 37° C.
Figure 3:
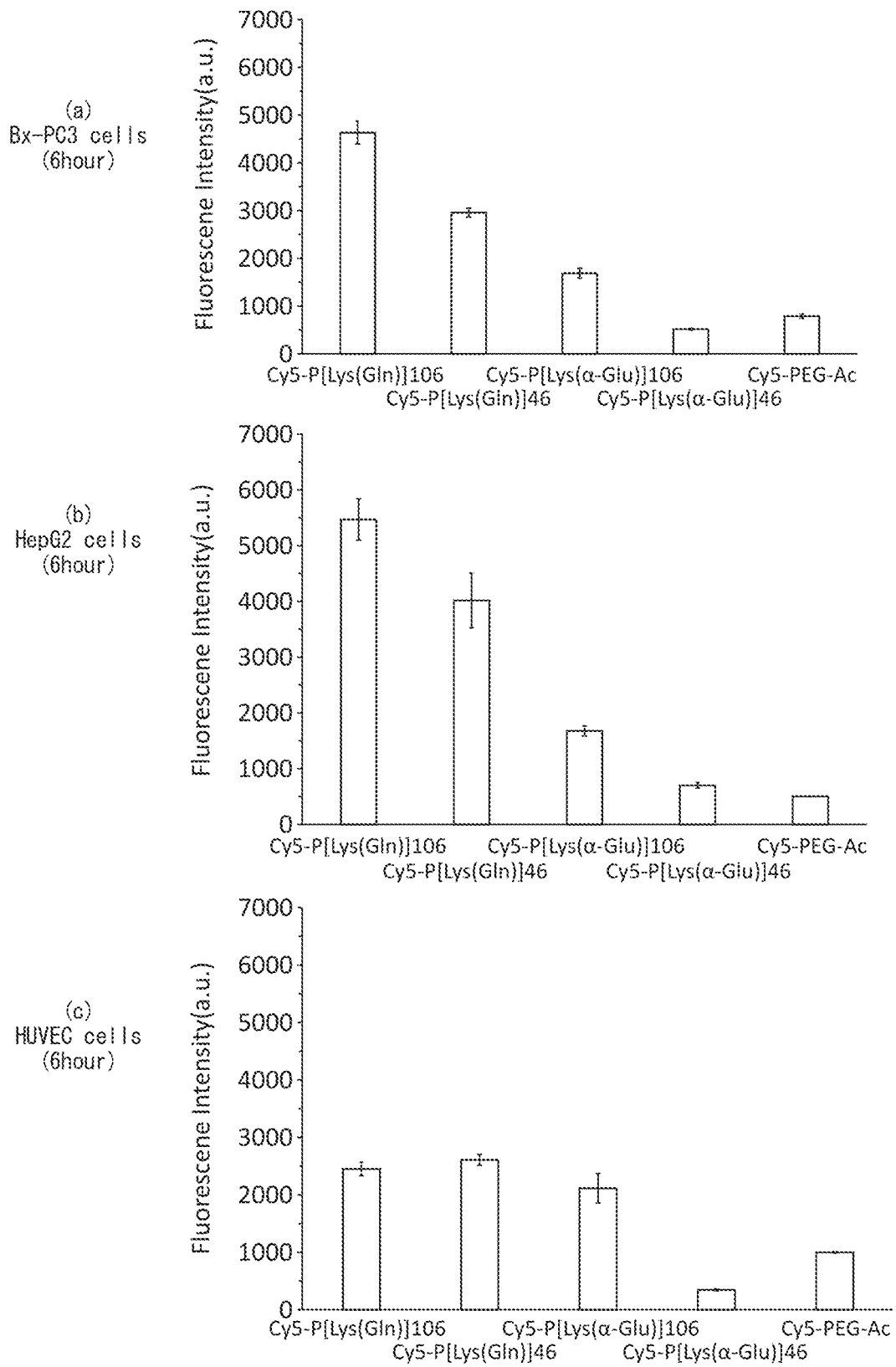
FIG. 3 depicts graphs showing a comparison of the amounts of polymer ligands taken up by cells in the case of incubating for 6 hours (n=3 each). (a) Bx-PC3 cells, (b) HepG2 cells, (c) HUVEC cells, polymer ligand concentration: 10 μM, incubation temperature: 37° C.

The Bx-PC3 cells, HepG2 cells and HUVEC cells were suspended in their respective media (Bx-PC3 cells: RPMI medium, HepG2 cells: DMEM medium, HUVEC cells: EGM™-2 Bullet Kit™) to prepare cell suspensions of 1.25×10$^5$ cells/ml. 400 μl aliquots of these cell suspensions were seeded into the wells of a 24-well plate (5.0×10$^4$ cells per well) and incubated for 24 hours at 37° C. After removing the medium and washing once with PBS, 400 μl of Cy5-P[Lys(Gln)]n (n=46 and 106), Cy5-P[Lys(α-Glu)]n (n=46 and 106) and Cy5-PEG-Ac were respectively added at a concentration of 1 μM and incubated for 1 hour or 6 hours at 37° C. After incubating for the prescribed time, the solution was removed followed by washing twice with PBS, and after adding 150 μl of Trp and incubating for 7 minutes at 37° C., 150 μl of PBS+10% FBS were added followed by measurement with a flow cytometer (FCM). The results are shown in FIGS. 2 and 3.

In the case of having incubated for 1 hour, uptake of Cy5-P[Lys(Gln)]n (n=46 and 106) was greater in comparison with uptake of Cy5-P[Lys(α-Glu)]n (n=46 and 106) and Cy5-PEG-Ac for each of the cancer cells (Bx-PC3 cells and HepG2 cells) and normal cells (HUVEC cells).

In the case of having incubated for 6 hours, uptake of Cy5-P[Lys(Gln)]n (n=46 and 106) was greater in comparison with uptake of Cy5-P[Lys(α-Glu)]n (n=46 and 106) and Cy5-PEG-Ac in cancer cells (Bx-PC3 cells and HepG2 cells). On the other hand, in the normal cells (HUVEC cells), no difference was observed in uptake among these polymer ligands in contrast with the uptake of the polymer ligands in cancer cells. On the basis thereof, there was clearly determined to be a difference between uptake of normal cells and uptake of cancer cells.

Example 4

Changes in Intracellular Uptake of Polymer Ligand in Case of Adding Inhibitor

In this experiment, uptake of polymer ligand was evaluated by using two types of inhibitors consisting of Bzl-Ser, which is used as an inhibitor of system ASC transporters including ASCT2, and glutamine (Gln), which is used as an inhibitor of system N transporters.

Bx-PC3 cells were suspended in RPMI medium (while HepG2 cells were suspended in DMEM medium and HUVEC cells were suspended in EGM™-2 Bullet Kit™) to prepare cell suspensions of $1.25 \times 10^5$ cells/ml. 400 μl aliquots of the cell suspensions were seeded into the wells of a 24-well plate ($5.0 \times 10^4$ cells per well) and incubated for 24 hours at 37° C. After removing the medium and washing once with PBS, 350 μl of 50 mM Bzl-Ser solution and 50 mM Gln solution, obtained by dissolving in PBS+10% FBS, and PBS+10% FBS were respectively seeded to the plates and incubated for 1 hour at 37° C. 50 μl aliquots of Cy5-P[Lys(Gln)]46, Cy5-P[Lys(Gln)]106, Cy5-P[Lys(α-Glu)]46, Cy5-P[Lys(α-Glu)]106 and Cy5-PEG-Ac were added to each solution at a concentration of 0.3 mg/ml and incubated for 1 hour at 37° C. After incubating for the prescribed amount of time, the solution was removed followed by washing twice with PBS, and after adding 150 μl of Trp and incubating for 7 minutes at 37° C., 150 μl of PBS+10% FBS were added followed by measurement with a flow cytometer (FCM).

Figure 4:
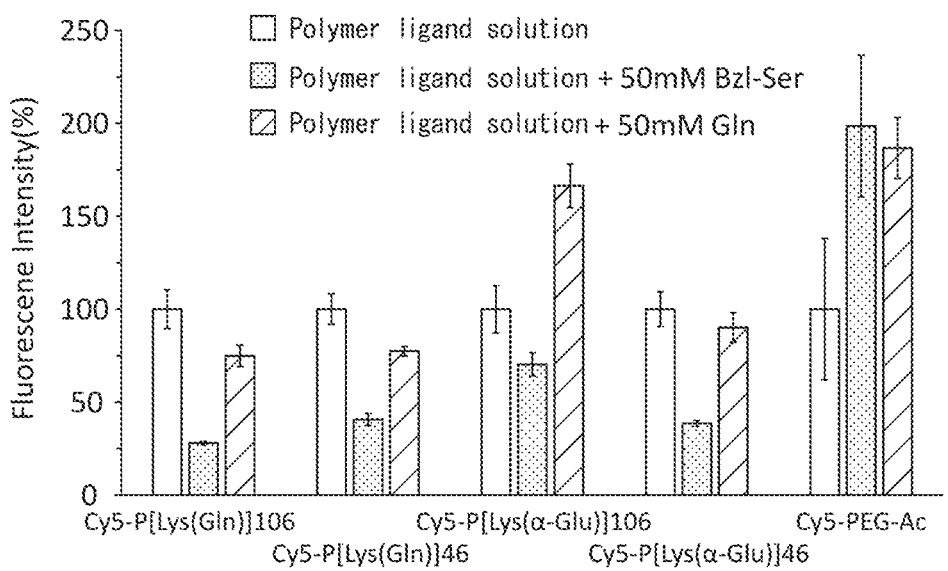
FIG. 4 is a graph showing the uptake rates of polymer ligands by Bx-PC3 cells in the presence or absence of inhibitor (n=3 each). Gln (Glu) concentration of polymer ligand side chain: 1 mM, temperature: 37° C., incubation time: 1 hr, calculated based on a value of 100% for uptake in polymer ligand solution.
Figure 5:
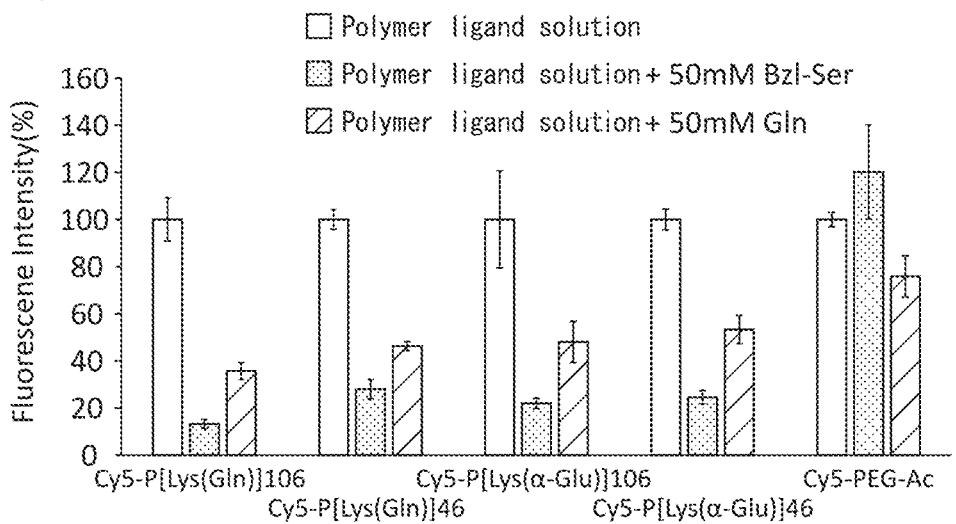
FIG. 5 is a graph showing the uptake rates of polymer ligands by HepG2 cells in the presence or absence of inhibitor (n=3 each). Gln (Glu) concentration of polymer ligand side chain: 1 mM, temperature: 37° C., incubation time: 1 hr, calculated based on a value of 100% for uptake in polymer ligand solution.
Figure 6:
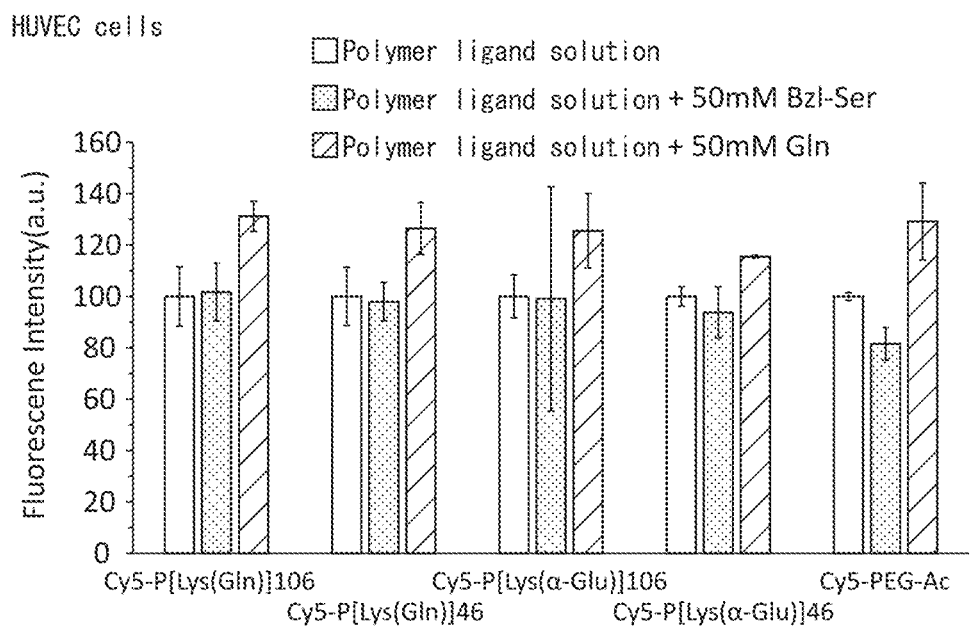
FIG. 6 is a graph showing the uptake rates of polymer ligands by HUVEC cells in the presence or absence of inhibitor (n=3 each). Gln (Glu) concentration of polymer ligand side chain: 1 mM, temperature: 37° C., incubation time: 1 hr, calculated based on a value of 100% for uptake in polymer ligand solution.

Changes in the uptake rates of ligands attributable to addition of inhibitor in the case of using BxPC3 cells, HepG2 cells and HUVEC cells are shown in FIGS. 4 to 6, respectively. Furthermore, uptake rates were calculated based on a value of 100% for fluorescence intensity during incubation of cells in polymer ligand solution.

Bzl-Ser binds to system ASC glutamine transporters such as ASCT2. In addition, Gln binds to system N glutamine transporters such as SNAT5. In the case of having added Bzl-Ser solution, uptake of Cy5-P[Lys(Gln)]46 and Cy5-P[Lys(Gln)]106 into cancer cells (Bx-PC3 cells and HepG2 cells) decreased considerably (FIGS. 4 and 5). In addition, in the case of having added Bzl-Ser solution, uptake of Cy5-P[Lys(α-Glu)]46, Cy5-P[Lys(α-Glu)]106 also decreased. On the other hand, in the case of having added Gln solution, ligand uptake did not decrease in comparison with the case of adding Bzl-Ser solution. In addition, in the case of Cy5-PEG-Ac, which is taken up into cells by non-specific adsorption, decreases in uptake were not observed both in the case of having added Bzl-Ser solution and in the case of having added Gln solution.

Example 5

Experiment on Inhibition of Polymer Ligand Uptake by Anti-ASCT2 Antibody (H-52)

Figure 7:
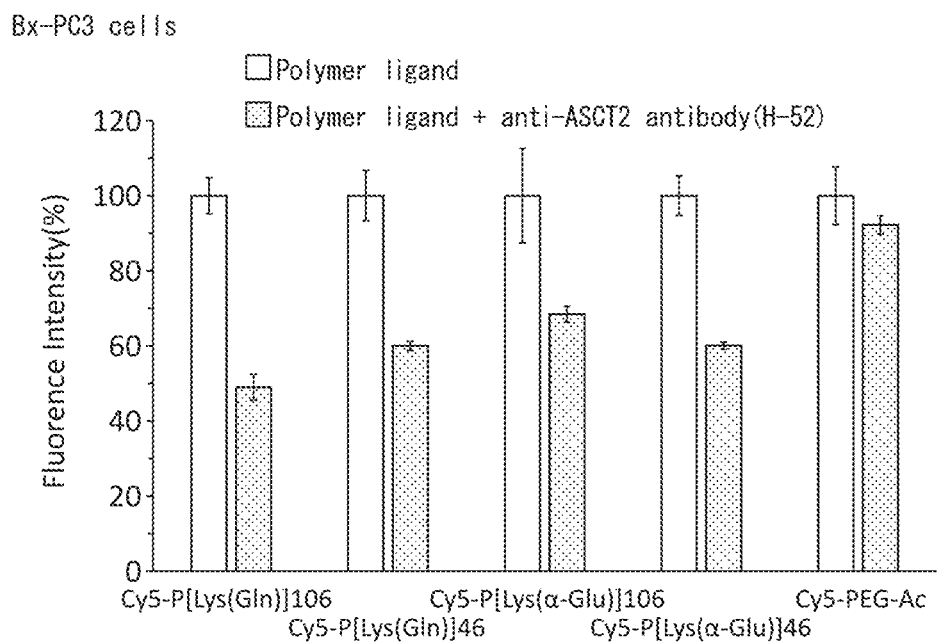
FIG. 7 is a graph showing the uptake rates of polymer ligands by Bx-PC3 cells in the presence or absence of anti-ASCT2 antibody (H-52) (n=3 each). Gln (Glu) concentration of polymer ligand side chain: 10 mM, temperature: 37° C., calculated based on a value of 100% for uptake of polymer ligand only.

Bx-PC3 cells were suspended in RPMI medium to prepare a cell suspension of $1.25 \times 10^5$ cells/ml. 400 μl aliquots of this cell suspension were seeded into the wells of a 24-well plate ($5.0 \times 10^4$ cells per well) and incubated for 24 hours at 37° C. After removing the medium and washing once with PBS, 160 μl aliquots each of antibody solution, obtained by diluting anti-ASCT2 antibody 1/25 times with PBS, and PBS were seeded into each well followed by incubating for 80 minutes at 37° C. Following incubation, 80 μl each of Cy5-P[Lys(Gln)]n (n=46 and 106), Cy5-P[Lys(α-Glu)]n (n=46 and 106) and Cy-PEG were added to each solution at 0.3 mg/ml and incubated for 1 hour at 37° C. After incubating for the prescribed amount of time, the solution was removed followed by washing twice with PBS, and after adding 150 μl of Trp and incubating for 7 minutes at 37° C., 150 μl PBS+10% FBS were added followed by passing through a cell strainer and measuring with a flow cytometer (FCM). The results are shown in FIG. 7.

Uptake of Cy5-P[Lys(Gln)]n (n=46 and 106) and Cy5-P[Lys(α-Glu)]n (n=46 and 106) was inhibited by anti-ASCT2 antibody (H-52). On the other hand, uptake was not inhibited for Cy-PEG, which is taken up into cells by non-specific adsorption. In addition, the reason for the inhibition rate of the anti-ASCT2 antibody (H-52) being lower than that of the system ASC transporter inhibitor, Bzl-Ser, is presumed to be that, since the anti-ASCT2 antibody (H-52) binds to a portion of ASCT2 instead of binding to the Gln recognition site of ASCT2, the ligand polymer is only subjected to conformational inhibition rather than inhibition of the recognition site. In actuality, there was no difference observed in antibody labeling between Bx-PC3 cells incubated in 50 mM Bzl-Ser solution and Bx-PC3 cells incubated in PBS+10% FBS.

Example 6

Changes in Intracellular Uptake at Low Temperature

Since Cy5-P[Lys(Gln)]n is a comparatively large molecule, it is presumed to be taken up into cells mainly by endocytosis after having bound to ASCT2 on the cell membrane. In order to confirm this, uptake of polymer ligand at a low temperature (4° C.), at which endocytosis is suppressed, was compared with uptake at 37° at which endocytosis proceeds normally.

Figure 8:
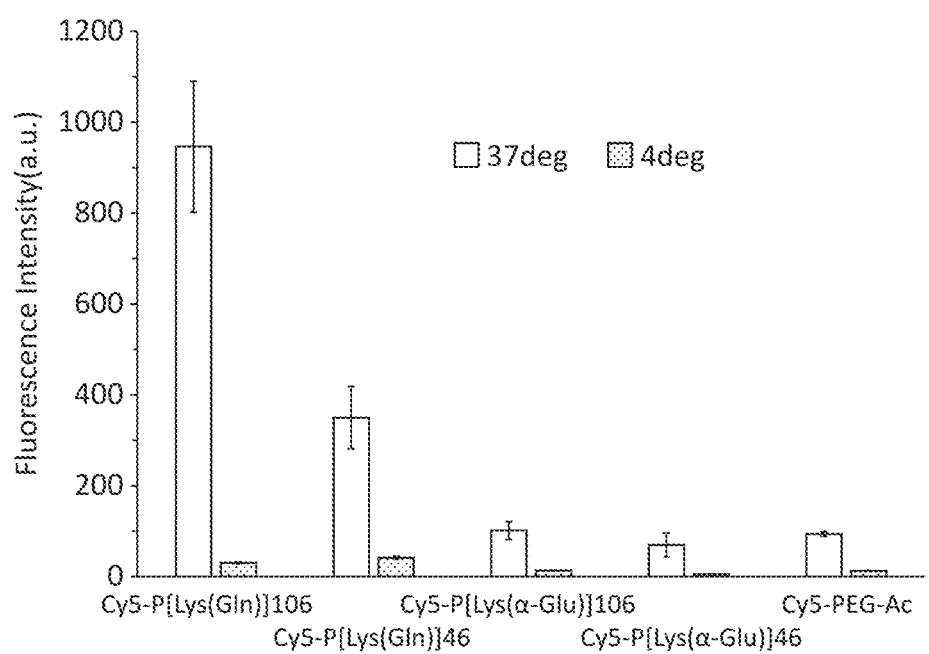
FIG. 8 is a graph showing the amounts of polymer ligands taken up by Bx-PC3 cells at 37° C. and 4° C. (n=3 each). Polymer ligand concentration: 10 μM.

Bx-PC3 cells were suspended in RPMI medium to prepare a cell suspension of $1.25 \times 10^5$ cells/ml. 400 μl aliquots of this cell suspension were seeded into the wells of a 24-well plate ($5.0 \times 10^4$ cells per well) and incubated for 24 hours at 37° C. After removing the medium and washing once with PBS, 400 μl of Cy5-P[Lys(Gln)]n (n=46 and 106), Cy5-P[Lys(α-Glu)]n (n=46 and 106) and Cy5-PEG-Ac were added at a concentration of 10 μM and incubated for 1 hour at 4° C. and 37° C. Furthermore, those wells incubated at 4° C. were allowed to stand undisturbed for 10 minutes at 4° C.

prior to removing the medium. After incubating for the prescribed amount of time, the solution was removed followed by washing twice with PBS, and after adding 150 µl of Trp and incubating for 7 minutes at 37° C., 150 µl of PBS+10% FBS were added followed by measuring with a flow cytometer (FCM). The results are shown in FIG. 8.

Uptake was confirmed to decrease considerably for all polymer ligands when incubated at 4° C. When cooled to 4° C., the action of ATP synthase is slowed and ATP-driven endocytosis is suppressed. Accordingly, polymer ligand bound to a transporter and the like on the surface of the cell membrane was suggested to be enclosed in a large vesicle with the entire cell membrane and then taken up mediated by endocytosis in which the polymer ligand is taken up into cells after having migrated into lysosomes starting in early endocytosis. Cy5-P[Lys(Gln)]n is presumed to be taken up into cells by endocytosis rather than being taken up by ASCT2.

Example 7

Evaluation of Intracellular Uptake in Case of Using Ligands Having Different Polymerization Degrees In this experiment, uptake was evaluated using Cy5-P[Lys(Gln)]25, Cy5-P[Lys(Gln)]46 and Cy5-P[Lys(Gln)]106 in order to evaluate the ability to be taken up into cells in the case of using ligands having different polymerization degrees.

Bx-PC3 cells were suspended in RPMI medium to prepare a cell suspension of $1.25 \times 10^5$ cells/ml. 400 µl aliquots of this cell suspension were seeded into the wells of a 24-well plate ($5.0 \times 10^4$ cells per well) and incubated for 24 hours at 37° C. After removing the medium and washing once with PBS, 400 µl each of Cy5-P[Lys(Gln)]n (n=25, 46, 106) and Cy5-P[Lys(α-Glu)]106 were added at 10 µM and incubated for 1 hour at 37° C. After incubating for the prescribed amount of time, the solution was removed followed by washing twice with PBS, and after adding 150 µl of Trp and incubating for 7 minutes at 37° C., 150 µl of PBS+10% FBS were added followed by measuring with a flow cytometer (FCM). An experiment using HepG2 cells was carried out in the same manner as described above with the exception of using DMEM medium. The results are shown in FIGS. 9 and 10.

A comparison between Cy5-P[Lys(Gln)]106 and Cy5-P[Lys(Gln)]46 revealed that there was greater uptake of Cy5-P[Lys(Gln)]106 having the higher degree of polymerization. On the other hand, a comparison of Cy5-P[Lys(Gln)]46 and Cy5-P[Lys(Gln)]25 revealed that there were no large differences observed between the uptake quantities of the two.

Example 7

Evaluation of Intracellular Uptake Using Confocal Laser Scanning Microscope (CLSM)

Uptake of polymer ligands into cells when changing the incubation temperature was evaluated using a CLSM. Bx-PC3 cells were suspended in RPMI medium to prepare a cell suspension of $1.25 \times 10^6$ cells/ml. 200 µl aliquots of this cell suspension were seeded into the wells of an 8-well glass dish ($1.0 \times 10^4$ cells per well) and incubated for 24 hours at 37° C. After removing the medium and washing once with PBS, 200 µl of Cy5-P[Lys(Gln)]106 was added at a concentration of 1 µM and incubated for 1 hour at 37° C. and 4° C. Furthermore, the dish incubated at 4° C. was allowed to stand undisturbed for 10 minutes at 4° C. prior to removing the medium. After incubating for the prescribed amount of time, the solution was removed followed by washing twice with PBS, and after adding 4% p-formaldehyde and allowing to stand undisturbed for 3 minutes, the p-formaldehyde was removed followed by washing once with PBS. After washing three times with TBST, 5% BSA was added followed by allowing to stand undisturbed for 10 minutes to carry out blocking. Following blocking, the dishes were washed once with PBS. Subsequently, 70 µl aliquots of anti-ASCT2 antibody solution diluted 50 times with 1% BSA were added to each well followed by allowing to stand undisturbed for 2 hours at room temperature. After removing the solution and going through three washings with PBS, 100 µl of DyLight® 488 solution diluted 800 times with PBS were added followed by allowing to stand undisturbed for 1 hour at room temperature. After removing the solution and going through three washings with PBS, Hoechst solution diluted 1000 times with PBS was added followed by allowing to stand undisturbed for 3 minutes at normal temperature. After removing the Hoechst solution and going through one washing with PBS, 200 µl of PBS and 1 drop of VectaShield were added followed by observation with the CLSM. CLSM observations were carried out using a 63× lens and detecting using wavelengths of 405 nm (Diode CW/Pulse), 488 nm (Ar laser) and 640 nm (HeNe laser). The resulting CLSM micrographs were converted to 3D models using IMALIS analytical software. The results are shown in FIGS. 11 to 14.

Figure 11:
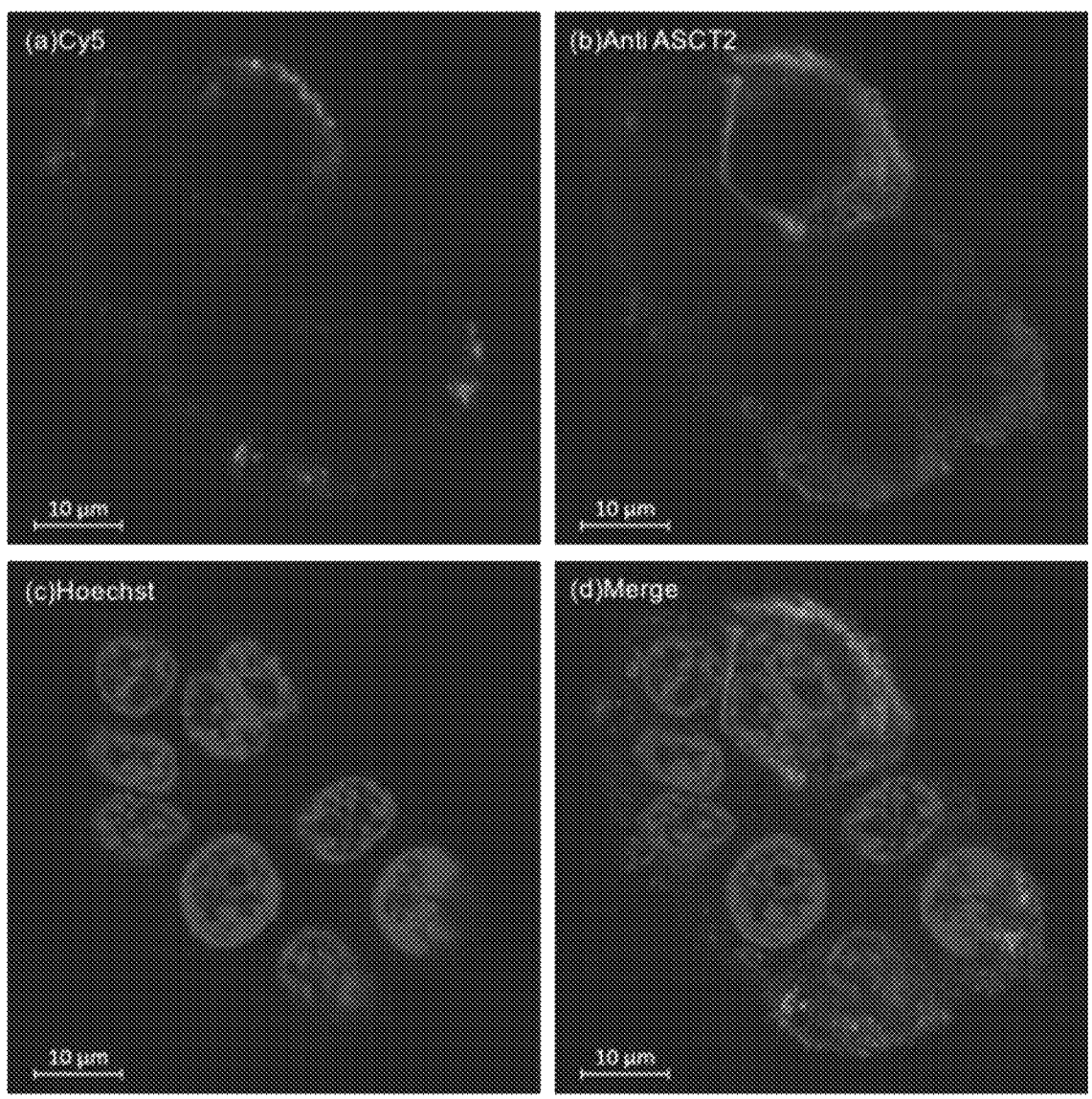
FIG. 11 depicts CLSM micrographs showing the uptake of Cy5-P[Lys(Gln)]106 into Bx-PC3 cells at 37° C. (a) Red: Cy5-P[Lys(Gln)]106 (Cy5), (b) Green: ASCT2 (DyLight 488), (c) Blue: cell nucleus (Hoechst), (d) Merge. Cy5-P[Lys(Gln)]106 concentration: 10 μM, incubation time: 1 hr, lens magnification factor: 63×.
Figure 12:
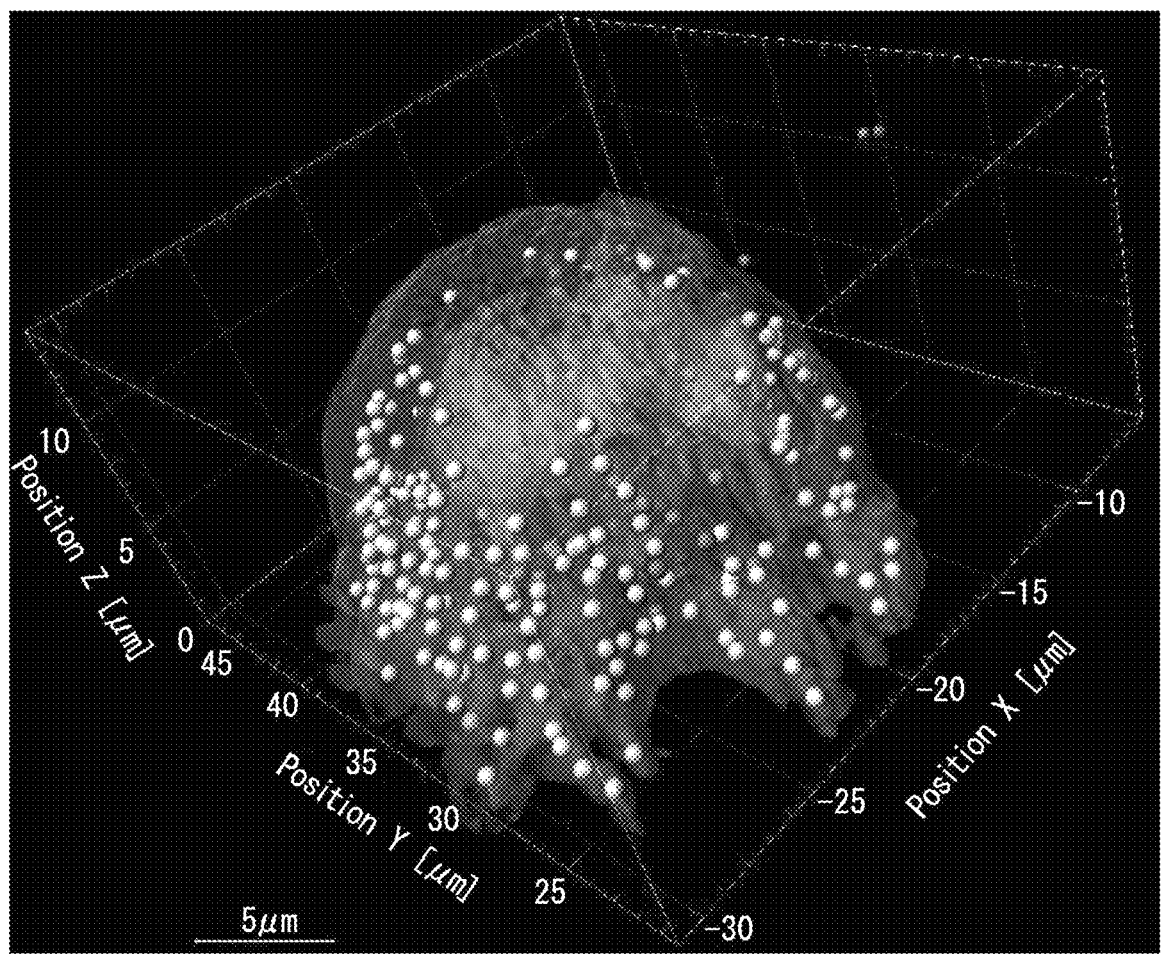
FIG. 12 is a 3D model showing uptake of Cy5-P[Lys(Gln)]106 into Bx-PC3 cells at 37° C. Red: Cy5-P[Lys(Gln)]106 (Cy5), Green: ASCT2 (DyLight 488), Blue: cell nucleus (Hoechst), Yellow: Delocalized portion of red and green.

At 37° C., the Cy5 (red) derived from Cy5-P[Lys(Gln)]106 was confirmed to be present within the cells (FIGS. 11 and 12). In addition, ASCT2 was confirmed to be distributed over the entire inside of the cell membrane based on the fluorescence (green) of a secondary antibody of anti-ASCT2 antibody in the form of DyLight® 488 (FIGS. 11 and 12).

Figure 13:
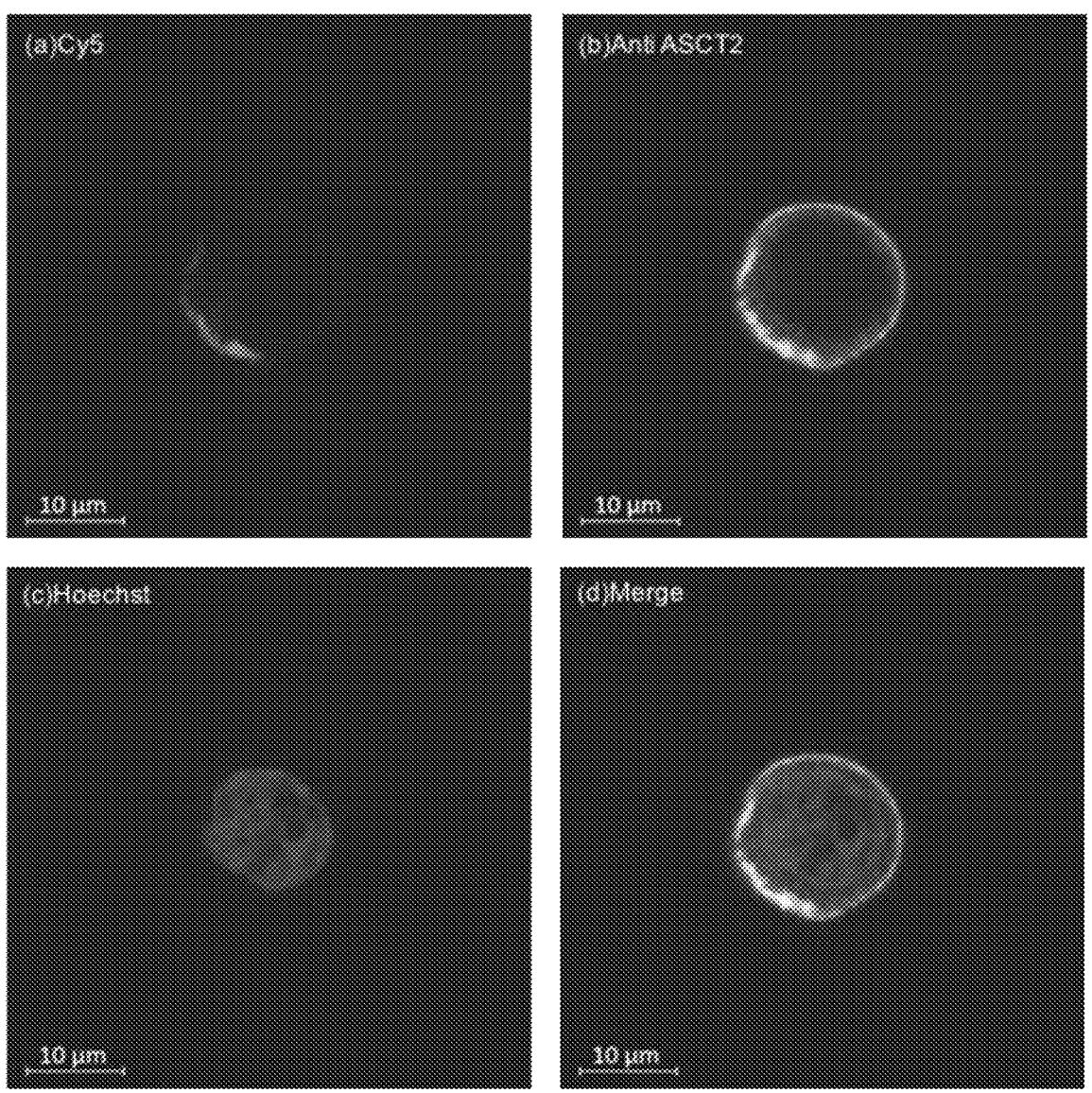
FIG. 13 depicts CLSM micrographs showing the uptake of Cy5-P[Lys(Gln)]106 into Bx-PC3 cells at 4° C. (a) Red: Cy5-P[Lys(Gln)]106 (Cy5), (b) Green: ASCT2 (DyLight 488), (c) Blue: cell nucleus (Hoechst), (d) Merge. Cy5-P[Lys(Gln)]106 concentration: 10 μM, incubation time: 1 hr, lens magnification factor: 63×.
Figure 14:
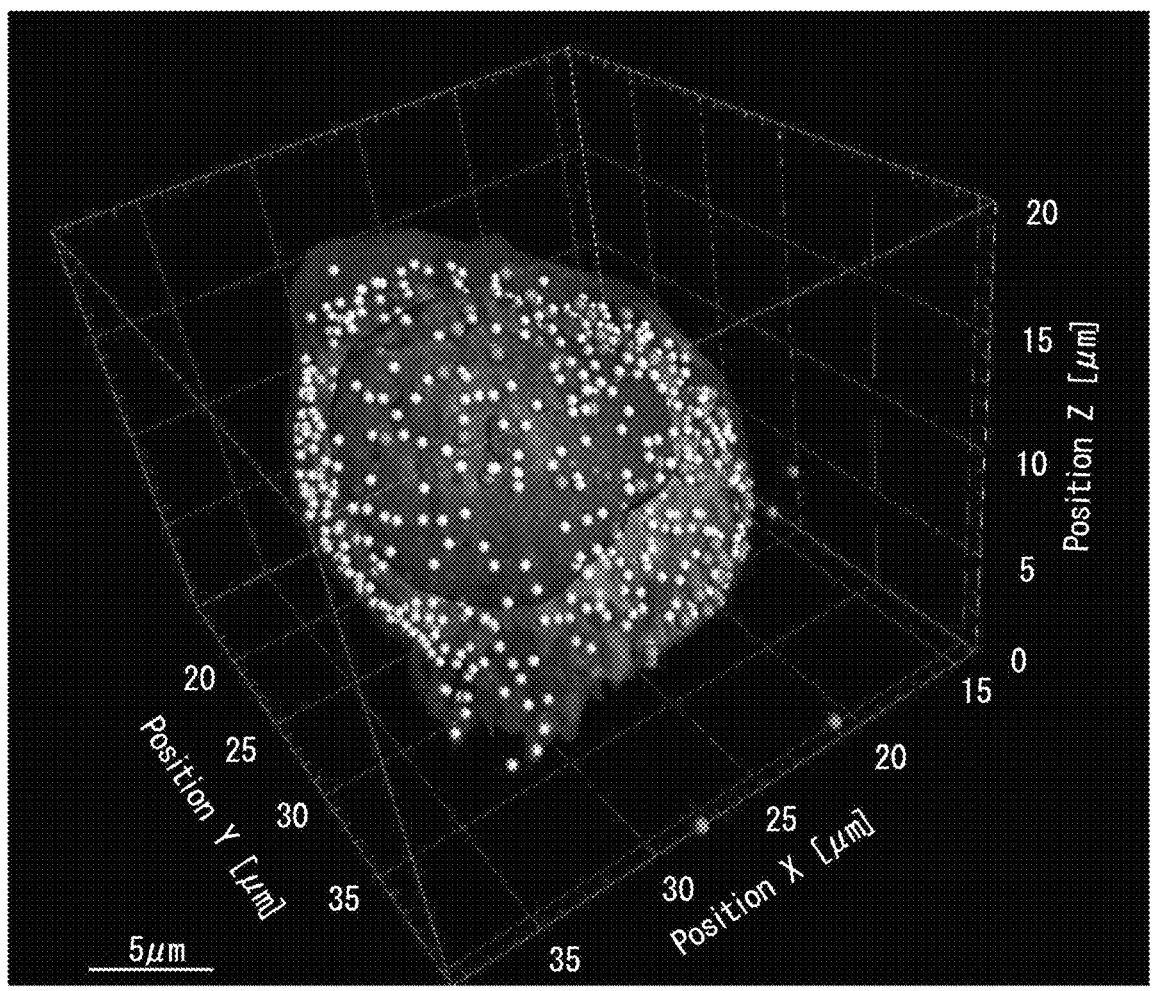
FIG. 14 is a 3D model showing uptake of Cy5-P[Lys(Gln)]106 into Bx-PC3 cells at 4° C. Red: Cy5-P[Lys(Gln)]106 (Cy5), Green: ASCT2 (DyLight 488), Blue: cell nucleus (Hoechst), Yellow: Delocalized portion of red and green.

At 4° C., Cy5 (red) derived from Cy5-P[Lys(Gln)]106 was confirmed to be present in large amounts on the cell surface. In addition, DyLight® 488 (green) derived from ASCT2 was confirmed to be present in large amounts on the surface of the cell membrane (FIGS. 13 and 14). On the basis of these results, endocytosis as well as uptake of Cy5-P[Lys(Gln)]106 are thought to be suppressed at 4° C.

Example 8

Evaluation of Tumor Retention Rates of Polymer Ligands

Figure 15:
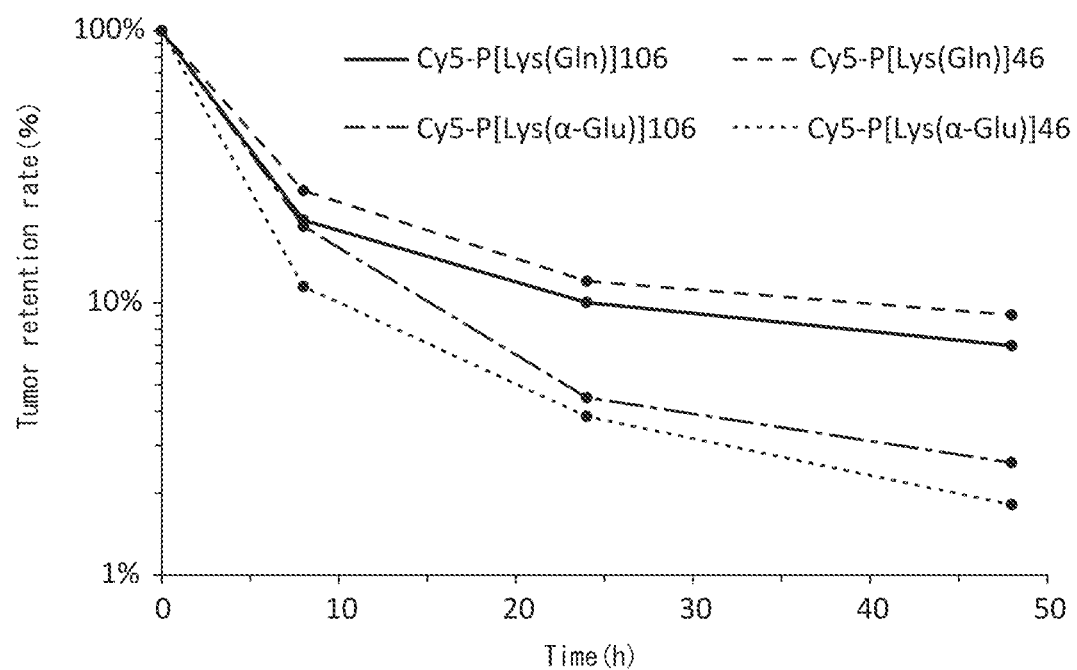
FIG. 15 is a graph showing changes in fluorescence intensity when polymer ligands were locally injected into a tumor of a mouse transplanted with Bx-PC3 cells (n=2). Polymer ligand concentration: 4 μM, fluorescence intensity at 30 minutes after administration of polymer ligand to tumor assigned value of 100% and taken to be starting point.
Figure 16:
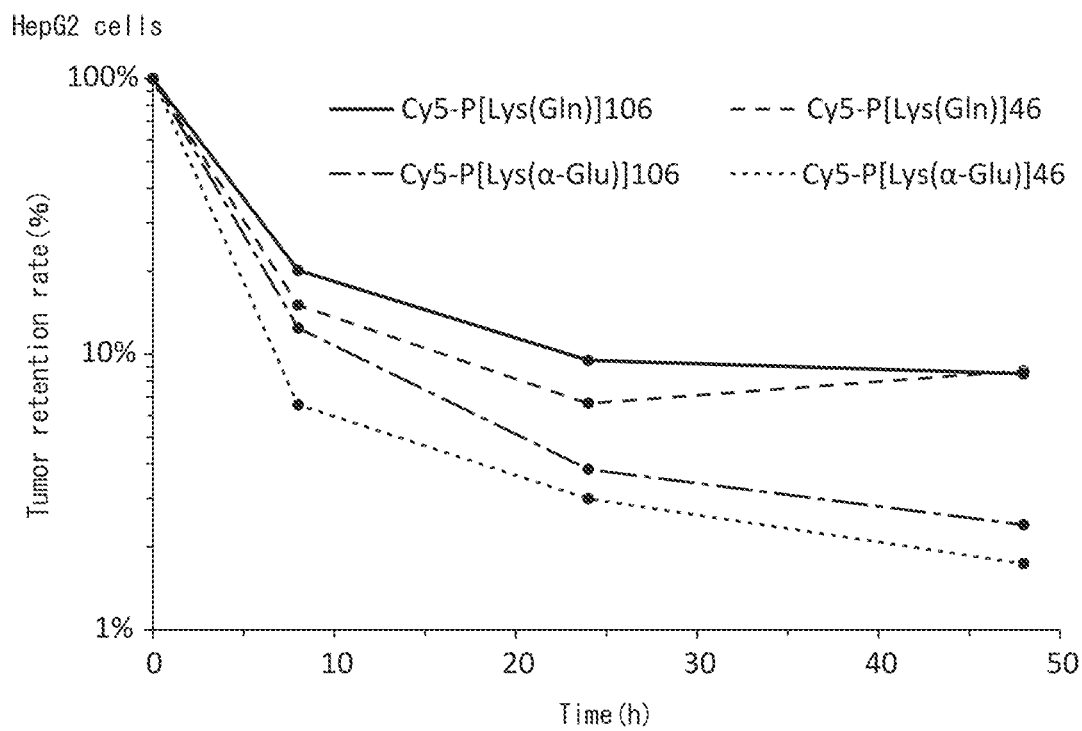
FIG. 16 is a graph showing changes in fluorescence intensity when polymer ligands were locally injected into a tumor of a mouse transplanted with HepG2 cells (n=2). Polymer ligand concentration: 4 μM, fluorescence intensity at 30 minutes after administration of polymer ligand to tumor assigned value of 100% and taken to be starting point.

Suspensions of BxPC3 cells and HepG2 cells were respectively subcutaneously transplanted into nude mice. The conditions of the cell suspensions consisted of a concentration of $1.0 \times 10^8$ cells/ml and volume of 50 µl. After the size of the tumors obtained by subcutaneous transplant of HepG2 and BxPC3 cells into the mice had grown to 200 mm³, 20 µl each of Cy5-P[Lys(Gln)]n (n=46, 106) and Cy5-P[Lys(α-Glu)]n (n=46, 106) at 40 µM, Cy5-P[Lys(Gln)]106 and Cy5-P[Lys(α-Glu)]106 at 1.2 mg/ml, and Cy5-P[Lys(Gln)]46 and Cy5-P[Lys(α-Glu)]46 at 0.6 mg/ml were respectively administered into the tumor portion. While defining the point at 30 minutes after administration as 0 hours, fluorescence intensity of the tumor portion was measured by IVIS after 0, 8, 24 and 48 hours. Fluorescence intensity was calculated from the radiant efficiency per area of the tumor portion (excitation wavelength: 640 nm, absorption wavelength: 700 nm). The results are shown in FIGS. 15 and 16.

Cy5-P[Lys(Gln)]n (n=46, 106) exhibited a higher tumor retention rate in comparison with Cy5-P[Lys(α-Glu)]n (n=46, 106) at 24 hours and beyond. Here, there were hardly any differences observed in tumor retention rates between Cy5-P[Lys(Gln)]106 and Cy5-P [Lys(Gln)] 46.

INDUSTRIAL APPLICABILITY

Use of the ligand of the present invention makes it possible to selectively target all types of cancer. Conjugating the ligand of the present invention with a drug enables the ligand of the present invention to be effectively used for cancer targeting therapy.

The invention claimed is:

1. A ligand capable of multivalently binding to a glutamine transporter that is expressed in excess in a cancer cell as compared with a normal cell, wherein the ligand comprising a polymer, wherein the polymer is represented by the following monomeric unit:

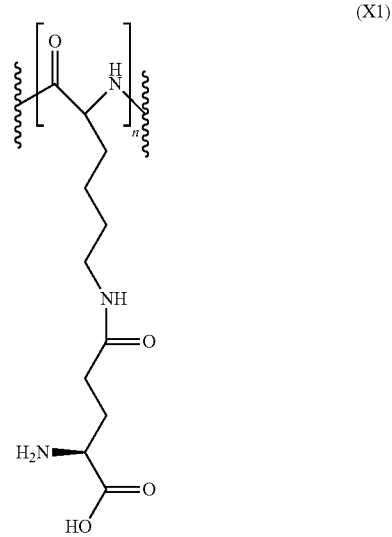

(X1)

wherein n represents an integer of 10 to 500.

2. The ligand according to claim 1, wherein the number average molecular weight of the ligand is 6000 Da to 70,000 Da.

3. The ligand according to claim 1, wherein the terminal primary amino groups of some of a plurality of groups represented by formula (X1) are capped with a protective group that is eliminated in a low pH environment.

4. The ligand according to claim 3, wherein the protective group that is eliminated in a low pH environment is selected from the group consisting of a phthaloyl group, maleoyl group, 2-carboxybenzoyl group and (2Z)-3-carboxy-2-propenoyl group.

5. The ligand according to claim 1, further comprising, wherein the ligand contains at least one detectable label or anticancer drug.

6. The ligand according to claim 5, wherein the at least one detectable label is selected from the group consisting of a fluorescent label; a luminescent label; a contrast agent; a detectable metal atom; a compound containing one or more detectable metal atoms; a radioisotope; a compound containing one or more radioisotopes; a detectable nanoparticle; and a detectable liposome.

7. The ligand according to claim 5, wherein the ligand is a compound represented by the following formula (4) or a pharmaceutically acceptable salt thereof:

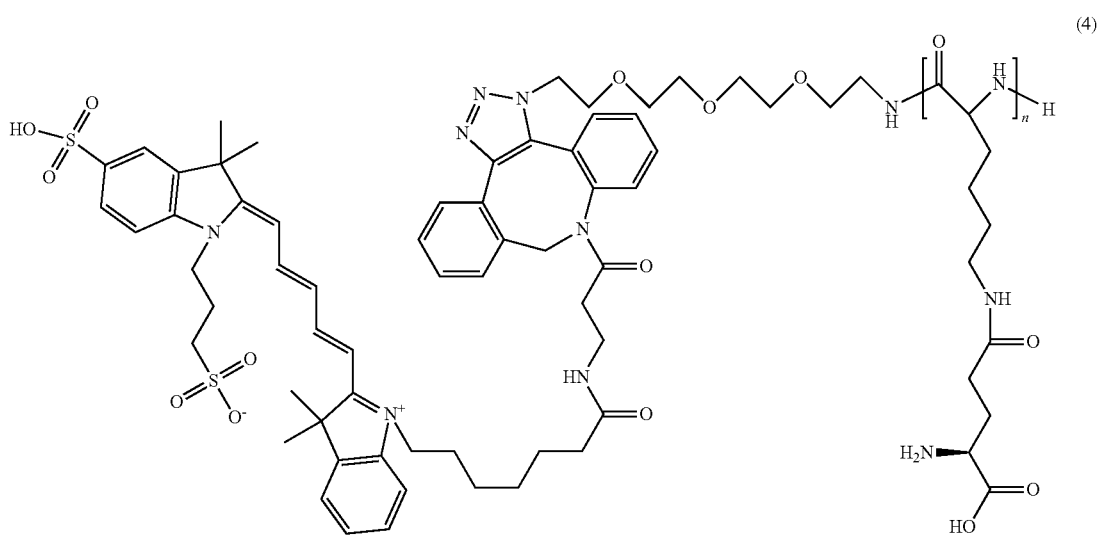

(4)

wherein n represents an integer of 10 to 500.

8. A composition comprising the ligand according to claim 1.

\* \* \* \* \*